United States Patent [19]

McAnalley et al.

[11] Patent Number: 5,773,425
[45] Date of Patent: Jun. 30, 1998

[54] ANTINEOPLASTIC USES OF ALOE PRODUCTS

[75] Inventors: Bill H. McAnalley, Grand Prairie; Robert H. Carpenter, Bastrop; Harley R. McDaniel, Dallas, all of Tex.

[73] Assignee: Carrington Laboratories, Inc., Irving, Tex.

[21] Appl. No.: 463,202

[22] Filed: Jun. 5, 1995

Related U.S. Application Data

[62] Division of Ser. No. 159,830, Dec. 1, 1993, Pat. No. 5,441,943, which is a division of Ser. No. 864,583, Apr. 7, 1992, Pat. No. 5,308,838, which is a division of Ser. No. 558,905, Jul. 27, 1990, Pat. No. 5,118,673, which is a continuation-in-part of Ser. No. 229,164, Aug. 5, 1988, Pat. No. 5,106,616, which is a continuation-in-part of Ser. No. 144,872, Jan. 14, 1988, Pat. No. 4,851,224, which is a continuation-in-part of Ser. No. 869,261, Jun. 5, 1986, Pat. No. 4,735,935, which is a continuation-in-part of Ser. No. 810,025, Dec. 17, 1985, abandoned, which is a continuation-in-part of Ser. No. 754,859, Jul. 12, 1985, abandoned, which is a continuation-in-part of Ser. No. 750,321, Jun. 28, 1985, abandoned, which is a continuation-in-part of Ser. No. 649,967, Sep. 12, 1984, abandoned, which is a continuation of Ser. No. 375,720, May 7, 1982, abandoned.

[51] Int. Cl.$^6$ .................................................. A61K 31/715
[52] U.S. Cl. ............................ 514/54; 514/883; 514/885
[58] Field of Search ............................ 514/54, 883, 885; 536/123.1

[56] References Cited

U.S. PATENT DOCUMENTS

| | | | |
|---|---|---|---|
| 4,735,935 | 4/1988 | McAnalley | 514/53 |
| 4,851,224 | 7/1989 | McAnalley | 424/195.1 |
| 5,106,616 | 4/1992 | McAnalley et al. | 424/85.2 |
| 5,118,673 | 6/1992 | Carpenter et al. | 514/54 |
| 5,308,838 | 5/1994 | McAnalley et al. | 514/54 |
| 5,441,943 | 8/1995 | McAnalley et al. | 514/54 |

Primary Examiner—John Kight
Assistant Examiner—Howard C. Lee
Attorney, Agent, or Firm—Hitt Chwang & Gaines, P.C.

[57] ABSTRACT

Methods for the treatment of sarcoma, carcinoma and lymphoma in an animal by administering to the animal an effective amount of a polymeric acetylated mannan derivative.

6 Claims, 2 Drawing Sheets

ANTINEOPLASTIC USES OF ALOE PRODUCTS

The present application is a divisional application of U.S. application Ser. No. 08/159,830, filed on Dec. 1, 1993, now U.S. Pat. No. 5,441,943, which is a divisional application of U.S. application Ser. No. 07/864,583, filed Apr. 7, 1992, now U.S. Pat. No. 5,308,838, which is a divisional application of U.S. application Ser. No. 07/558,905, filed Jul. 27, 1990, now U.S. Pat. No. 5,118,673, which in turn, is a continuation-in-part of U.S. application Ser. No. 07/229,164, filed Aug. 5, 1988, now U.S. Pat. No. 5,106,616, and entitled "Administration of Acemannan," the entire contents and disclosure of which are hereby specifically incorporated by reference. Said U.S. application Ser. No. 07/229,164 corresponds to International Application PCT/US89/03381, filed Aug. 3, 1989, and published under International Publication No. WO 90/01253 on Feb. 22, 1990, the entire contents and disclosure of which are also hereby specifically incorporated by reference. The said U.S. application Ser. No. 07/229,164 is a continuation-in-part of U.S. application Ser. No. 07/144,872, filed Jan. 14, 1988, and entitled "Process for Preparation of Aloe Products," granted on Jul. 25, 1989, as U.S. Pat. No. 4,851,224, the entire contents and disclosure of which are hereby specifically incorporated by reference. Said U.S. Pat. No. 4,851,224 is a continuation-in-part of U.S. application Ser. No. 06/869,261, filed on Jun. 5, 1986, and entitled "Processes for Preparation of Aloe Products, Products Produced Thereby and Compositions Thereof," granted on Apr. 5, 1988, as U.S. Pat. No. 4,735,935, the entire contents and disclosure of which are also hereby specifically incorporated by reference. Said U.S. Pat. No. 4,735,935, corresponds to International Application No. PCT/US86/01335, filed Jun. 20, 1986, and published under International Publication No. WO 87/00052 on Jan. 15, 1987, the entire contents and disclosure of which are also hereby specifically incorporated by reference. Said U.S. Pat. No. 4,735,935 is a continuation-in-part of U.S. application Ser. No. 06/810,025, filed Dec. 17, 1985 (now abandoned), which is a continuation-in-part of U.S. application Ser. No. 06/754,859, filed Jul. 12, 1985 (now abandoned) which is a continuation-in-part of U.S. application Ser. No. 06/750,321 filed Jun. 28, 1985 (now abandoned), which is a continuation-in-part of U.S. application Ser. No. 06/649,967 filed Sep. 12, 1984 (now abandoned), which is a continuation of U.S. application Ser. No. 06/375,720 filed May 7, 1982 (now abandoned). Application Ser. No. 06/810,025 is entitled "Processes for Preparation of Aloe Products and Products Produced Thereby." Applications Ser. Nos. 06/754,859; 06/750,321; 06/649,967; and 06/375,720 are entitled "Process for Preparation of Aloe Vera Products."

BACKGROUND OF THE INVENTION

1. Field of the Invention

The invention pertains to uses of biological response modifying agents. More particularly, this invention relates to the therapeutic use of a polysaccharide substance which is predominantly an acetylated mannan or its derivatives to:

1) relieve the symptoms and/or cure the viral diseases of animals, including humans, other mammals, and birds, as well as of plants. These polysaccharidic substances inhibit viral replication either alone, or in combination with other drugs, either through direct antiviral effects or through their immune stimulating activities;

2) enhance the response of the immune system to cancer in humans, other mammals, animals, birds and plants. These polysaccharidic substances stimulate immune cells of the body and directly alter the tumor cell surface so that the stimulated immune cells now recognize the tumor cells as "not self";

3) alter the body's response to antigens, toxins, allergens and "self" antigens as seen in autoimmune diseases. These polysaccharidic substances cause immune regulator cells to function more appropriately to achieve homeostasis;

4) act as adjunctive therapy with other drugs in a wide range of conditions where the final step in resolution or cure of the condition requires an immune response. These polysaccharidic substances can be used with anti-infective, antitumor, anti-inflammatory, and anti-depressant drugs with no toxicity due to the polysaccharidic substance. The efficacy of the combination is superior over the single drug alone.

2. Description of the General Background Information

Aloe is a member of the lily family. Harding, *Aloes of the World: A Checklist. Index and Code, Excelsa* 9:57–94 (1979). *Aloe barbadensis* Miller is generally recognized as the "true aloe" because of its wide use and, reportedly, most effective healing power, although in Japan, *Aloe arborescens* Miller traditionally has been used as a folk remedy for various ailments ranging from gastrointestinal disorders to athlete's foot. Aloe vera is a perennial plant with turgid green leaves joined at the stem in a rosette pattern. The leaves of a mature plant may be more than 25 inches long with sawlike spikes along their margins.

Aloe vera contains two major liquid sources, a yellow latex (exudate) and the clear gel (mucilage). The dried exudate of *Aloe barbadensis* Miller leaves is referred to as aloe. The commercial name is Curacao aloe. It is composed mainly of aloin, aloe-emodin and phenols. Bruce, *South African Medical Journal.* 41:984 (1967); Morrow et al., *Archives of Dermatology*,116:1064–1065 (1980); Mapp et al., *Planta Medica*, 18:361–365 (1970); Rauwald, *Archives Pharmazie*, 315:477–478 (1982). A number of phenolics, including anthraquinones and their glycosides, are known to be pharmaceutically active. Bruce, *Excelsa*, 5:57–68 (1975); Suga et al., *Cosmetics and Toiletries*, 98:105–108 (1983).

The mucilaginous jelly from the parenchymal cells of the plant is referred to as Aloe vera gel. There are generally no anthraquinones to decompose and cause discoloration of the gel unless the gel is contaminated by an improper processing technique. Aloe vera gel is about 98.5% water by weight. More than 60% of the total solid is made up of polysaccharides of carbohydrate origin. Organic acids and inorganic compounds, especially calcium oxalate, account for the remainder of the solid.

Whole leaves, exudates and fresh gels of Aloe plants have been used for a variety of human afflictions. Evidence of their use as a medicinal remedy can be traced to the Egyptians of 400 BC. Aloe vera was also used to embalm the dead, as well as to protect the embalmers from the death-causing agent. Other early civilizations used Aloe vera for skin care, to relieve insect stings and bites, to treat scratches and ulcerated skin, to promote wound healing, to prevent hair loss and as a purgative. It was the traditional medicine of many cultures as an anthelmintic, cathartic and stomachic and was used inter alia for leprosy, burns and allergic conditions. Cole et al., *Archives of Dermatology and Syphilology*, 47:250 (1943); Chopra et al., *Glossary of Indian Medicinal Plants*, Council of Scientific and Industrial Research, New Delhi (1956); Ship, *Journal of the American Medical Association*, 238(16):1770–1772 (1977); Morton, *Atlas of Medicinal Plants of Middle American Bahamas to*

*Yucatan*, Charles C. Thomas Publisher, 78–80 (1981); Diez-Martinez, La Zabila, *Communicado NO. 46 Sobre Recursos Bioticos Potenciales del Pais*, INIREB, Mexico (1981); Dastur, *Medicinal Plants of India and Pakistan*: D.B. Taraporevala Sons & Co., Private Ltd., Bombay 16–17 (1962).

Aloe vera has enjoyed a long history of lay acceptance as possessing "curative" or "healing" qualities. Over the last few years, numerous books and articles meeting scientific standards have been written on Aloe vera. Organizations such as the Aloe Vera Council and recognized medical institutions, through publications and case histories of physicians, veterinarians and other scientists, have given credence to the "aloe phenomenon." Aloe vera has been featured extensively in the field of dermatology, especially for treating radiation-caused skin conditions. Mackee, *X-rays and Radium in the Treatment of Diseases of the Skin*, 3rd Ed., Lea and Febiger, Philadelphia, 319–320 (1938); Rovatti et al., *Industrial Medicine and Surgery*, 28:364–368 (1959); Zawahry et al., *Quotations From Medical Journals on Aloe Research*, Ed. Max B. Skousen, Aloe Vera Research Institute, Cypress, Calif., 18–23 (1977); Cera et al., *Journal of the American Animal Hospital Association*, 18:633–638 (1982). The body of scientific literature documenting medical applications in digestive problems, as a virucidal, bactericidal and fungicidal agent and in gynecological conditions is extensive and has been adequately reviewed by Grindley et al., [*Journal of Ethnopharmacology*, 16:117–151 (1986)].

Depending on the way the leaves are processed, mucilage and sugars are the major components of the dehydrated gel. The sugars found are galactose, glucose, mannose, rhamnose, xylose and uronic acids. Although reports conflict, the mucilage is mainly composed of mannan or glucomannan. Eberendu et al., *The Chemical Characterization of Carrisyn®* (in preparation); Mandal et al., *Carbohydrate Research*, 86:247–257 (1980b); Roboz et al., *Journal of the American Chemical Society*, 70:3248–3249 (1948); Gowda et al., *Carbohydrate Research*, 72:201–205 (1979); Segal et al., *Lloydia*, 31:423 (1968).

Prior to this work, the controversy over the identity of the active substance(s) in Aloe vera had not been settled. It is therefore important to clearly distinguish between the components present in the gel and those found in the exudates. A majority of the gel is a mucilage of mainly polysaccharide nature with minor amounts of various other compounds. It has been observed that in some of the activities there may be some synergistic action between the polysaccharide base and other components. Leung, *Excelsa* 8:65–68 (1978); Henry, *Cosmetics and Toiletries*, 94:42–43, 46, 48, 50 (1979). For example, several workers report that the effective components for wound healing may be tannic acid [Freytag, *Pharmazie*, 9:705 (1954)] and a kind of polysaccharide. Kameyama, Wound-healing compositions from Aloe arborescens extracts. Japanese Patent#7856995, (1979). Mackee, supra, noted that the gel, not the rind or the exudate, was responsible for the beneficial effects in the treatment of radiation burns, and he stressed the importance of using fresh leaves for effective treatment. Polysaccharides degrade with time, and certain molecular weight sizes may be necessary to elicit a specified pharmacological response. Goto et al., *Gann*, 63:371–374 (1972).

However, there are many examples in the literature indicating that polysaccharides can exhibit pharmacological and physiological activities without help from other components. Gialdroni-Grassi, *International Archives of Allergy and Applied Immunology*, 76(Suppl. 1):119–127 (1985); Ohno et al., *Chemical and Pharmaceutical Bulletin*, 33(6): 2564–2568 (1985); Leibovici et al., *Chemico-Biological Interactions*, 60:191–200 (1986); Ukai et al., *Chemical and Pharmaceutical Bulletin*, 31:741–744 (1983); Leibovici et al., *Anticancer Research*, 5:553–558 (1985). One such example relates to development of atherosclerosis. Hyperlipidemia in the general population and especially in familial hypercholesterolemia is associated with coronary heart disease and death. In countries where dietary fiber intake is high, atherosclerosis appears to be uncommon. Trowell et al., Editors, *Refined Carbohydrate Foods and Disease*, London, Academic Press, 207 (1975). Pectin and guar are reported to lower cholesterol in normal and hyperlipidemic patients. Kay et al., *American Journal of Clinical Nutrition*, 30:171–175 (1977). Locust bean gum, a polysaccharide composed of mannose and galactose, decreased the plasma lipoprotein cholesterol concentrations in both normal and familial hypercholesterolemic subjects. Zavoral et al., *American Journal of Clinical Nutrition*, 38:285–294 (1983). Addition of guar gum to carbohydrate meals decreased the postprandial rise of glucose in both normal and diabetic subjects. Jenkins et al., *Lancet*, 2:779–780 (1977). Kuhl et al., in *Diabetes Care*, 6(2):152–154 (1983) demonstrated that guar gum exhibited glycemic control of pregnant insulin-dependent diabetic patients.

The antitumor activity of polysaccharides has been widely reported. Polysaccharides prepared from *Lentinus cyathiformis* are known to increase host defense against tumors. Rethy et al., *Annales Immunologiae Hungaricae*, 21:285–290 (1981). There are several reports that polysaccharides from mushroom, yeast or bacterial extracts can elicit a high degree of host defense activity against viral and tumor infestations. Chihara, *Nature*, 222:687 (1969); Shwartzman et al., *Proceedings of the Society for Experimental Biology and Medicine*, 29:737–741 (1932);

Suzuki et al., *Journal of Pharmacobio-Dynamics*, 7(7): 492–500 (1984), also reported antitumor activity of a polysaccharide fraction (GF-1) extracted from cultured fruiting bodies of a fungus, *Grifola frondosa*. This fraction showed equivalent, high levels of inhibiting activity when administered intraperitoneally (IP), intravenously (IV) and intratumorally (IT). However, oral administration (PO) was not effective. The GF-1 fraction also exhibited antitumor action against the solid form of Meth A fibrosarcoma and MM 46 carcinoma in mice. Lentinan, which is a 6-branched $\beta$-1-3-linked glucan similar to GF-1, was ineffective against Meth A fibrosarcoma. Chihara, "The antitumor polysaccharide Lentinan: an overview;" *Manipulation of Host Defense Mechanisms*; Ed. by Aoki et al., *Excerpta Medica*, North Holland, 1–16 (1981); Sasaki et al., *Carbohydrate Research*, 47(1):99–104 (1976). Synthesized branched polysaccharides were reported to demonstrate activities against tumors. Matsuzaki et al., *Makromol. Chem.*, 186(3):449–456 (1985). Matsuzaki et al. [*Makromol. Chem.*, 187(2):325–331 (1986)] synthesized branched polysaccharides, which showed significant activities, from ivory nut mannan ($\beta$-(1-4)-D-mannopyranose) and $\beta$-(1-4)-linked glucomannan. A partially acetylated linear $\beta$-(1-3)-D-mannan extracted from fruit bodies of *Dictyophoria indusiata* Fisch, also exhibited antitumor activity. Hara, *Carbohydrate Research*, 143:111 (1982). It appears that antitumor action depends on the type of polymer main chain and its degree of polymerization, because $\beta$-(1-3)-glucan-type polymers show higher antitumor activity than $\beta$-(1-4)-glucan and hemicellulosic polymers. Matsuzaki et al., *Makromol. Chem.*, 187:325–331 (1986). A carboxymethylated derivative of $\beta$-(1-3)-glucan obtained from bacterial culture filtrate caused severe cell loss from established sarcoma 180 tumors within 2 hours after the injection of the derivative. Baba, *Journal of Immunopharmacology*, 8(6):569–572 (1986). The same author observed a compensatory increase in polymorphonuclear leukocytes due to injection of the substance. Incidentally, bestatin, a dipeptide known to possess immunemodulating and antitumor activity [Ishizuka, *Journal of Antibiotics*, 32:642–652 (1980)], influenced neither the tumor yield nor the polymorphonuclear leukocyte count. Baba et al., supra.

There are numerous reports on the antitumor effect of sulfated polysaccharides, including heparin [Jolles et al., *Acta Univ. Int. Cancer*, 16:682–685 (1960); Suemasu et al., *Gann*, 61(2):125–130 (1970)], sulfated laminaran and dextran [Jolles et al., *British Journal of Cancer*, 17:109–115 (1963)]. Yamamoto et al., in *Japanese Journal of Experimental Medicine*, 54:143–151 (1984), reported enhancement of antitumor activity of a fucoidan fraction by further sulfation. The sulfated product demonstrated activity against L-1210 leukemia. The authors postulated that the mechanism of the antitumor action might be due partly to inhibition of. invasive growth of L-1210 cells, as a result of electrostatic repulsion between the tumor cell and mesothelial cells. Yamamoto et al., supra. Polysaccharides with sulfate groups are also reported to be human T cell mitogens and murine polyclonal B cell activators. Sugawara et al., *Microbiological Immunology*, 28(7):831–839 (1984). Generally, homopolysaccharides of high molecular weight with sulfate groups possess these properties. Dorries, *European Journal of Immunology*, 4:230–233 (1974); Sugawara et al., *Cell Immunology*, 74:162–171 (1982).

It has been reported that glucan extracted from the yeast *Saccharomyces cervisiae* is a modulator of cellular and humoral immunity. Wooles et al., *Science*, 142:1078–1080 (1963). The polysaccharide also stimulated proliferation of murine pluripotent hematopoietic stem cells, granulocyte macrophage colony-forming cells and cells forming myeloid and erythroid colonies. Pospisil et al., *Experientia*, 38:1232–1234 (1982); Burgaleta, *Cancer Research*, 37:1739–1742 (1977). Maisin et al., [*Radiation Research*, 105:276–281 (1986)] also reported that IV administration of a polysaccharide induced protection of murine hematopoietic stem cells against x-ray exposure, thereby decreasing the mortality of the mice so exposed.

Lackovic et al., [*Proceedings of the Society for Experimental Biology and Medicine*, 134:874–879 (1970)], took yeast cell-wall and extracted all constituent matter leaving only "mannans" that he found to be responsible for the induction of α-interferon production by monocytes. The "purified mannans" alleged to be responsible for the physiologic response had a molecular weight of 5,500–20,000 daltons. He theorized that mannans stimulated mouse peritoneal macrophages to produce the λ-interferon. He also stated that the mannans he isolated showed no toxicity and "they are poor antigens." There was no mention by Lackovic et al. of the use of these "purified mannans" for antiviral activity or for IL-1 stimulation. We submit that Lackovic et al.'s "purified mannans" comprised an assortment of unknown and unidentified substituted and unsubstituted mannans.

Seljelid et al., [*Experimental Cell Research*, 131(1): 121–129 (1981)] have observed that insoluble or gelforming glycans activated macrophages in vitro, whereas the corresponding soluble glycans did not. They postulated that the orientation in which the glycan was presented to the mononuclear phagocyte was decisive for activation. Bogwald, [*Scandinavian Journal of Immunology*, 20:355–360 (1984)] immobilized glycans that had a stimulatory effect on the macrophages in vitro. This led the authors to believe that the spatial arrangement of the glycan was decisive for the effect on the macrophages in vitro. A purified polysaccharide isolated from *Candida albicans* induced an antibody response by human peripheral blood lymphocytes in vitro. Wirz et al., *Clinical Immunology and Immunopathology*, 33:199–209 (1984). There were significant differences between the antiCandida and Candida antibodies in sera of normal and infected individuals. Wirz et al., supra.

The antiviral activity of polysaccharides and polysaccharides linked to peptides has been observed. Suzuki et al., *Journal of Antibiotics*, 32:1336–1345 (1979). Suzuki et al., supra, reported an antiviral action of peptidomannan (KS-2) extracted from mycelial culture of *Lentinus edodes*. Both oral and intraperitoneal administration increased the peak serum interferon titer, which protected mice against viral infections. This was different from dextran phosphate (DP-40) [Suzuki et al., *Proceedings of the Society for Experimental Biology and Medicine*, 149(4):1069–1075 (1975)] and 9-methylstreptimidone (9-MS) [Saito et al., *Antimier. Agent & Chemotherapy*, 10(1):14–19 (1976)], which induced higher titers of interferon in mice only if administered IV or IP.

Anti-inflammatory activity of Aloe vera gel has been widely reported by both oral testimonies and respected scientific journals. Rubel [*Cosmetics and Toiletries*, 98:109–114 (1983)] discussed fully the possible mechanism of the anti-inflammatory effect of aloe gel. Ukai et al., [*Journal of Pharmacobio-Dynamics*, 6(12):983–990 (1983)] noted anti-inflammatory activity of polysaccharides extracted from the fruiting bodies of several fungi. The polysaccharides demonstrated a significant inhibitory effect on carrageenan-induced edema. One of the polymers, O-acetylated-D-mannan (T-2-HN), in addition demonstrated a more marked inhibitory effect than phenylbutazone on scald hyperalgesia. Ukai et al., supra. The assertion that the polysaccharide is free from protein and lipids strongly suggests that the anti-inflammatory effect is due to the acetylated mannan only.

Other researchers have also reported anti-inflammatory effects of complex polysaccharides [Saeki et al., *Japanese Journal of Pharmacology*, 24(1):109–118 (1974)], glycoproteins [Arita et al., *Journal of Biochemistry*, 76(4):861–869 (1974)] and sulfated polysaccharides [Rocha et al., *Biochemical Pharmacology*, 18:1285–1295 (1969)].

Literature which reports that polysaccharides possess pharmacological and physiological activities continues to flood the pages of well-respected scientific journals. It is therefore logical that the mucilaginous gel of the Aloe vera plant, which is essentially a polysaccharide, holds the secret to Aloe vera's medicinal properties. The controversy over whether the polysaccharide is a glucomannan, mannan, pectin, or of some other composition, is resolved by a series of chemical purification steps. Yagi et al., [*Planta Medica*, 31(1):17–20 (1977)], using a slightly modified extraction method; isolated acetylated mannan (aloe mannan) from *Aloe arborescens* Miller var. *natalensis*. Ovodova [*Khim. Prior. Soedin*, 11(1):325–331 (1975)], however, earlier isolated pectin as the main component of the same aloe species.

As discussed above, the biological activity of polysaccharides has been recognized for many years. Polysaccharide materials recovered from plants, yeast and bacteria have demonstrated direct biological activity by eliciting an increase in host defense systems. This reaction is primarily manifested by increased host surveillance for other antigenic substances. Polysaccharides serve as adjuvants (DEAE Dextran, etc.) and immunomodulators. They also can function as unique T cell-independent antigens. Both cellular and humoral immunity may be affected, and increased phagocytosis of infectious organisms and tumor cells has been observed, as has enhanced production of immunoglobulins.

The structure of these immunologically active polysaccharides and the types of structural variations appear to be the factors that control their potency and toxicity. Their mode(s) of action remain poorly understood; however, recent evidence indicates that several polysaccharides induce lymphocytes and macrophages to produce a wide range of immunologically active substances. For example, 2-keto-3-deoxy-D-manno-octulosonic acid (KDO) appears to be the chemical portion of lipopolysaccharide (LPS) that provides the minimum signal for macrophage host defense activation [Lebbar et al., *Eur. J. Immunol*, 16(1):87–91 (1986)]. The composition of the present invention possesses all of the attributes of these immunologically active substances; it is among the most potent of all known biologically active polysaccharides but differs in that no toxicity has been observed. It also manifests specific antiviral activity through alteration of viral glycoprotein synthesis.

A number of pharmacology studies have been conducted on Aloe vera gel in recent times. Results have included more rapid healing of radiation burns [Rowe, *J. Am. Pharm. Assoc.*, 29:348–350 (1940)] and accelerated healing of wounds [Lushbaugh et al., *Cancer*, 6:690–698 (1953)]. Thermal burns treated with Aloe vera gel heal much faster than untreated burns [Ashley et al., *Plast. Reconstr. Surg.*, 20:383–396 (1957), Rovatto, supra, Rodriguez-Bigas et al., *J.Plast. Reconstr. Surg.*, 81:386–389 (1988)]. The gel is useful in treating leg ulcers [El Zawahry et al., *Int. J. Dermatol.*, 12:68–73 (1973)] and in hastening post surgical healing (Payne, Thesis submitted to Faculty of Baylor University, Waco, Tex., MS Degree). Experimental evidence suggests that extracts of Aloe vera have anti-infectious properties [Solar, *Arch. Inst. Pasteur Madagascar*, 47:9–39 (1979)] and enhance phagocytosis [Stepanova, *Fiziol. Akt. Veshchestva*, 9:94–97 (1977)].

The active fraction of Aloe vera gel has been identified by Carrington Laboratories, Inc., Irving, Tex., as a long-chain polydisperse β-(1,4)-linked acetylated mannan interspersed with O-acetyl groups having a mannose monomer-to-acetyl group ratio of approximately 1:0.91. Acemannan is the nonproprietary name of the biologically active component of Carrisyn®, a compound isolated and developed by Carrington Laboratories, Inc. See U.S. Pat. No. 4,735,935, U.S. Pat. No. 4,851,224, and the U.S. patent application Ser. No. 07/229,164, and references cited therein, the disclosures of all of which are incorporated herein by reference. All of these patents and this patent application are also assigned to Carrington Laboratories, Inc.

Mannans, including glucomannans and galactomannans, have long been used by man. For example, galactomannans, in the form of plant gums, are widely employed as binders for control of food texture. In addition, some mannans have exhibited significant therapeutic properties (Davis and Lewis, eds. Jeanes A., Hodge J., In: American Chemical Society Symposium, Series 15. Washington, DC, American Chemical Society, 1975). Practitioners of Japanese folk medicine have long believed that extracts of certain fungi have anticancer activity. On investigation, many of these extracts have been found to contain complex carbohydrates with immune-stimulating activity. These carbohydrates are usually polymers of mannose (mannans), glucose (glucans), xylose (hemicellulose), fructose (levans) and mixtures of these. Individual sugars may be bonded in different ways and chains may be branched or unbranched. Glucans have been the most widely studied of these immunostimulatory carbohydrates. It has become increasingly clear that even though they have no toxicity mannans are as effective, if not more effective, than glucans.

Pure mannans are relatively uncommon in higher plants, although they are a major structural component of some yeasts. For example, about 45% of the cell wall of *Saccharomyces cerevisiae* consists of a mannan. This mannan is a water soluble molecule composed of β-(1,6)-, β-(1,3)-, and β-(1,2)-linked, partially phosphorylated D-mannose residues [McMurrough et al., *Biochem.J.*, 105:189–203 (1967)]. Other biologically active mannans have been obtained from *Candida utilis* [Oka et al., *Gann*, 60:287–293 (1969), Oka et al., *Gann*, 58:35–42 (1968)], *Candida albicans, Coccidioides immitis* and *Rhodotorulum rubrum* [Wheat et al., *Infect. Immun.*, 41:728–734, (1983)]. Mannans (including galactomannans and glucomannans) are relatively resistant to attack by mannosidases but can be degraded by exo- and endomannanases [Emi, et al., *Agr. Biol. Chem.*, 36:991–1001 (1972), Snaith, et al., *Adv. Carbohydr. Chem. Biochem.*, 28:401–445, (1973) Herman, *Am. J. Clin. Nutr.*, 24:488–498 (1971), McMaster, et al., *Proc. Soc. Exp. Biol. Med.*, 135:87–90 (1970), Jones et al., *J. Biol. Chem.*, 243:2442–2446 (1968), Eriksson et al., *Acta. Chem. Scand.*, 22:1924–1934 (1968)]. The most marked biological activities of mannans in mammals are activation of macrophages and stimulation of T cells. As a result, they are potent immunostimulants with significant activity against infectious diseases and tumors [Hasenclever et al., *J. Immun.*, 93:763–771 (1964)].

Saccharomyces mannan (15 mg/kg/day) enhances carbon clearance in normal male ddI mice, presumably acting as a reticuloendothelial system stimulant [Suzuki et al., *Gann*, 62:553–556 (1971)]. This same mannan also increases the number of antibody-forming cells in the spleen [Suzuki et al., *Gann*, 62:343–352 (1971)]. In vitro studies with mouse peritoneal cells (a mixture of macrophages and lymphocytes) indicate that some mannans and mannan-protein complexes can stimulate interferon release both in vivo and in vitro [Lackovic et al., *Proc. Soc. Exp. Biol, Med.*, 134:874–879 (1970)]. The mannans stimulated interferon release in a manner similar to endotoxins but, in contrast to endotoxins, caused minimal toxicity (Borecky et al., *Acta Virol.*, 11:264–266 (1967), Hasenclever, supra). The mannan from *Candida albicans* is active in this way, but the mannan from *Saccharomyces cerevisiae* is inactive [DeClercq et al., *Ann. NY Acad. Sci.*, 173:444–461 (1970)]. Inconsistent or poor results have been obtained in other laboratories (DeClercq, supra). These differences may be due to slight structural or size differences in the polymers [Suzuki et al., *Jpn. J. Microbiol.*, 12:19–24 (1968)]. The latter is more likely responsible since low molecular weight mannans (5.5–20 kDa) tend to be most active in the interferon-inducing assay, also Saccharomyces mannan tends to be larger than Candida mannan.

A galactomannan of 20 kDa from *Lipomyces starkeyi* had weak interferon-inducing properties. In contrast, *Candida albicans* mannan induced the appearance of interferon activity 2–24 hrs after intravenous administration (Borecky, supra).

DMG, a degraded mannoglucan from *Microellobosporia grisea* culture fluid, can stimulate cytotoxic activities of macrophages, natural killer (NK) cells and killer T cells, and it enhances the secretion of interleukin-1 (IL-1) and colony-stimulating factors (CSF). It has more potent antitumor activity than lentinan (a glucan from *Lentinus edodes*) [Nakajima et al., *Gann*, 75:260–268, (1984), Inoue et al., *Carbohyd. Res.*, 114:164–168 (1983)]. DMG stimulates macrophages to produce increased amounts of IL-1. In addition, DMG enhances 1) antibody production against sheep erythrocytes, 2) natural killer activity of spleen as well as of peritoneal cells, and 3) cytostatic activity of peritoneal macrophages [Nakajima et al., *Gann*, 75:253–259 (1984)].

Mannose-binding proteins have been identified in the serum of rabbits and in the liver of humans and laboratory rodents. These proteins can bind glucomannans such as those found in cell walls of bacteria, yeasts, fungi and in envelope glycoproteins of certain viruses such as the human immunodeficiency virus (HIV). In humans, the major mannose-binding protein is an acute-phase protein; its levels rise in stressed individuals [Ezekowitz et al., *J. Exp. Med.*, 169:185–196 (1989)]. The envelope glycoproteins of the human immunodeficiency virus (HIV gp120 and gp41) contain mannose-rich oligosaccharides that appear to be potential ligands for the mannose-binding protein. As a result, the mannose-binding protein can inhibit HIV infection of lymphoblasts and bind selectively to HIV-infected cells. Free yeast mannan can competitively interfere with binding of this protein to infected cells. Thus, factors that induce an increase in the level of the mannose-binding protein may confer protection against HIV.

PROBLEMS TO WHICH THE INVENTION IS ADDRESSED

Virus, cancer and diseases of immune regulation continue to be major causes of both morbidity and mortality in humans, other mammals, other animals, birds, and plants. Problems associated with currently used drugs are, namely, general toxicity, lack of efficacy (or both), deficiency in specificity and development of resistance by causative organisms or agents. Hence, better non-toxic yet therapeutically efficient agents are needed for the treatment of these diseases. Acemannan has been shown to possess a unique combination of immunodulatory and antiviral properties.

SUMMARY OF THE INVENTION

It is therefore an object to provide a method of enhancing or stimulating the immune system in an animal, comprising the administration of an amount of acetylated mannan derivative sufficient to effect the enhancement and the stimulation of the immune system in the animal.

It is also an object to provide a method of activating, inducing, and/or enhancing in an animal the synthesis and production of cytokines (such as interleukins, interferon, and prostaglandin) by monocytes and macrophages, peripheral blood adherent cells, comprising the administration of an amount of an acetylated mannan derivative to the animal sufficient to effect monocyte and macrophage activation.

It is a further object to provide a method of stimulating macrophage phagocytosis in an animal, comprising the administration of an amount of an acetylated mannan derivative sufficient to effect monocyte and macrophage activation.

It is still a further object to provide a method of producing an antiviral effect in a tissue culture, animal, or plant, comprising the administration of a sufficient amount of an acetylated mannan derivative into the tissue culture, animal, or plant to produce the antiviral effect.

It is still a further object to provide a method of producing defective virus in a human infected with virus, comprising the administration of an amount of an acetylated mannan derivative into the human sufficient to effect monocyte and macrophage activation and alter viral replication in cells infected with virus.

It is another object to provide a method of producing an antiviral effect in an animal, comprising the administration of an amount of an acetylated mannan derivative into the animal sufficient to induce interferon synthesis, enhance antibody formation, enhance T-cell activities, enhance killer cell activities, stimulate thymic activity, alter glycosylation of glycoprotein, alter second messenger synthesis and activity, inhibit viral replication, or a combination of any of the above.

It is still a further object to provide a method of producing defective virus in a master seed culture for vaccine production, comprising adding a predetermined amount of an acetylated mannan derivative into the master seed culture sufficient to produce altered viral replication.

It is still a further object to provide a method of stimulating and enhancing cytokine synthesis by cells of the immune system, comprising the administration of an amount of an acetylated mannan derivative into the animal sufficient to stimulate cytokine synthesis.

It is yet another object of the present invention to provide a method of inducing the immune system of a plant or an animal to inhibit the growth of a tumor or a cancer, comprising the administration of a sufficient amount of an acetylated mannan derivative into the plant or the animal to cause the immune system of the plant or animal to inhibit the growth of a tumor or a cancer.

It is also an object of the present invention to provide a method of causing the immune system of a plant or an animal to destroy or inhibit the growth of a tumor or a cancer, comprising the administration of a sufficient amount of an acetylated mannan derivative into the plant or animal to cause the immune system of the plant or animal to recognize the tumor or cancer as "not self."

It is a further object of the present invention to provide a method of producing anticancer effects in animals that have succumbed to cancer of viral, chemical, radiation, genetic or other origins.

It is still a further object to provide a method of producing an antitumor effect in an animal that has succumbed to tumors of genetic origins, comprising the administration of an amount of an acetylated mannan derivative into the animal sufficient to inhibit primary and secondary messenger expression of oncogenes.

It is yet another object to provide a method of reducing tissue damage, such as ulceration and/or necrosis, and of restoring soft-tissue capillary bed vascular perfusion in an animal, comprising the administration of an amount of an acetylated mannan derivative into the animal sufficient to restore tissue viability.

It is also an object to provide a method of reducing the symptoms associated with inflammatory bowel diseases in an animal, comprising the administration of an amount of an acetylated mannan derivative into the animal sufficient to reduce the symptoms associated with inflammatory bowel disease.

It is further an object to provide a method of reducing symptoms associated with multiple sclerosis in a human, comprising the administration of an amount of acetylated mannan derivative into the human sufficient to reduce symptoms associated with multiple sclerosis.

It is also an object to provide a method of reducing the symptoms associated with neurochemical disorders and depression in an animal, comprising the administration of an amount of acetylated mannan derivative into the animal sufficient to reduce the symptoms associated with neurochemical disorders and depression.

It is a further object to provide a method of treatment of acute and chronic autoimmune disease in an animal, comprising the administration of an acetylated mannan derivative into the animal sufficient to cause immunosuppression and/or immunomodulation of the cells and tissues responsible for the autoimmune disease.

It is still a further object to provide a method of causing a more rapid healing of traumatic injuries in an animal, comprising the administration of an acetylated mannan derivative into the animal sufficient to cause the animal's body tissue repair mechanism and immune system to respond more rapidly and appropriately to a trauma.

It is a further object to provide a method of causing an affect on the respiratory system of an animal to ameliorate the symptoms associated with asthma, conjunctivitis, rhinitis and bronchitis, comprising the administration of an acetylated mannan derivative into the animal sufficient to cause immunomodulation of the cells and tissues responsible for the symptoms associated with asthma, conjunctivitis, rhinitis and bronchitis.

It is still a further object to provide a method of producing a prophylactic effect in an animal resulting in the prevention of infection by infectious organisms, comprising administration of an acetylated mannan derivative into the animal sufficient to cause the animal body's immune system to prevent infection by an infectious organism.

It is also an object to provide a method of reactivating enzyme systems and organ systems to cause a return to function of age-depleted tissue, comprising the administration of an acetylated mannan derivative into the animal sufficient to cause the animal body and its tissue to produce cell products and up-regulate genes which cause the tissue to return to function and express juvenile cell function and characteristics.

It is a still further object to provide a method of immunoenhancing vaccines by the production of an adjuvant effect, comprising adding a predetermined amount of an acetylated mannan derivative into the vaccine product.

It is a still further object to provide a method of treating an animal afflicted with a tumor, comprising administration to the animal an amount of an acetylated mannan derivative sufficient to effect monocyte and macrophage activation and enhance natural killer cell activity and specific tumor cell lysis by cytotoxic cells and/or antibodies.

It is a still further object to provide a method of introducing an acetylated mannan derivative into the cellular organelles of (i) a noninfected cell to give rise to altered glycoproteins which provide said cell with protection from viral infection and/or of (ii) a virus-infected cell to produce glycoproteins which destroy or inhibit viral expression in said infected cell, comprising introducing a sufficient amount of an acetylated mannan derivative into the cell to alter viral glycoproteins in or at the surface of the cell.

It is still a further object to provide a method of introducing an acetylated mannan derivative into the cellular organelles of a virus-infected cell to produce glycoproteins which prevent or inhibit viral expression in said infected cell wherein the acetylated mannan derivative is introduced into the cell in an amount sufficient to render the virus noninfective.

It is a still further object to provide a method of introducing an acetylated mannan derivative into the cellular organelles of a virus-infected cell to produce altered glycoproteins which prevent or inhibit viral expression in said infected cell wherein the cell is virus-infected, comprising the administration of the acetylated mannan derivative into the cell in an amount sufficient to (i) to cause a broad spectrum of specific antibodies to be produced which provide a broader immunological response than the cell had prior to introduction, and (ii) to enhance the rate of broad spectrum antibody production.

It is also an object of this invention to provide a method of increasing, in an animal, amounts of acetylated mannan derivative to intra- and extra-cellular metabolic pathways to correct malabsorption and mucosal cell maturation syndromes in an animal, comprising the step of administration to the animal an amount of the acetylated mannan derivative sufficient to provide additional acetylated mannan derivative for the synthesis of glycoprotein thus accelerating Michaelis-Menten ($K_m$) kinetics for mannosyl transferase activity.

It is a further object to provide a method of inducing a virus-infected mammalian cell to express altered viral glycoprotein antigens on its surface which will initiate an antibody-dependent cell cytolysis (ADCC) by cytotoxic lymphocytes, comprising administration to the mammal an amount of an acetylated mannan derivative into the infected cell sufficient to produce altered viral glycoproteins and to cause the altered viral glycoproteins to be expressed on the surface of the infected cells and thus expose them to humoral antibodies.

It is still another object to provide a method of introducing an acetylated mannan derivative into a human to reduce the symptoms associated with multiple sclerosis, comprising administration to the human an amount of the acetylated mannan derivative sufficient to reduce plaque formation and to induce plaque replacement with functional tissue in the central nervous system cells.

It is also an object to provide a method of introducing an acetylated mannan derivative into a mammal to reduce the symptoms associated with inflammatory bowel disease, comprising the administration to the mammal an amount of the acetylated mannan derivative sufficient to resolve lesions associated with inflammatory bowel disease by increasing tissue regeneration of ulcers in said lesions and by reducing autoimmune immunoglobulin in local tissues of said lesions.

DETAILED DESCRIPTION OF PREFERRED EMBODIMENTS

Figure 1:
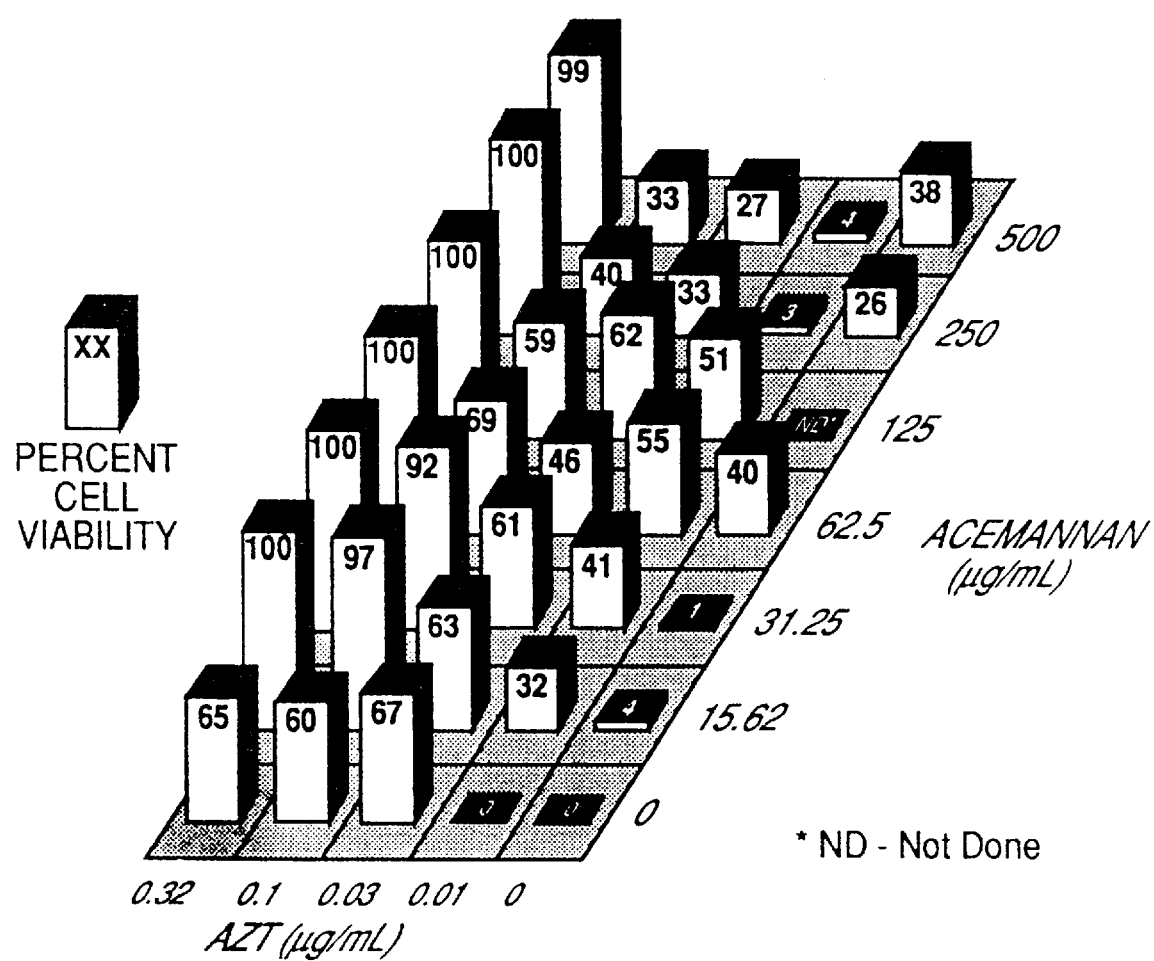
FIG. 1 shows synergistic antiviral effects of acemannan and AZT on the viability of HIV-infected MT-2 cells.

Carrisyn® is the brand name given by the assignee of the instant invention to the purified ethyl alcohol extract of the inner gel of the leaves of *Aloe barbadensis* Miller. The active component of Carrisyn®g has been designated "acemannan" by the United States Adopted Name Council. Not less than 73% of Carrisyn® extract is acemannan; Carrisyn® extract comprises generally about 73% to 90% acemannan. Carrisyn® extract is generally produced by removing the outer sheath of the leaf, then removing and processing the inner filet or mucilage as follows: pH adjustment, ethanol extraction, freeze drying and grinding. See U.S. application Ser. No. 144,872 filed January 1988, a continuation-in-part of U.S. application Ser. No. 869,261 (now U.S. Pat. No. 4,735;935), the disclosures of all of which are incorporated herein by reference. Processing in this manner predicts that essentially no covalent bonds are altered and therefore no toxic compounds are created. These manufacturing steps were developed to overcome the inability of traditional aloe product producers to standardize and stabilize the polysaccharides.

Carrisyn is a fluffy, white, amorphous powder, which is poorly soluble in water and dimethyl sulfoxide and insoluble in most other organic solvents. This powder contains not less than 73% of a polysaccharide consisting essentially of linear β(1-4)-D-mannosyl units. The polysaccharide is a long chain polymer interspersed randomly with acetyl groups linked to the polymer through an oxygen atom. The generic name for the polymer is acemannan. The degree of acetylation is approximately 0.91 acetyl groups per monomer as determined by the alkaline hydroxamate method. See Hestrin, *Journal of Biological Chemistry*, 180:240–261 (1949). Neutral sugars linkage analysis indicates that attached to the chain, probably through an α(1-6) linkage, is a D-galactopyranose in the ratio of approximately one for every 70 sugars. The 20:1 ratio of mannose to galactose indicates that galactose units are also linked together, primarily by a B(1–4) glycosidic bond. The chemical structure of acemannan may be represented as follows:

General Structure of Ultrapure Acemannan

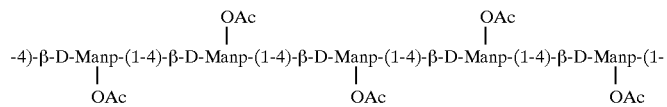

p = Pyranose

DEFINITION OF TERMS

The term "virus" as used herein includes both the DNA and the RNA virus. It can either be an enveloped or a non-enveloped virus. The term "enveloped virus" in all cases but one is understood to mean a virus encased within a modified host cell membrane; the poxviruses produce their own envelope. Typical enveloped viruses are set forth in Table 1.

TABLE 1

The following are enveloped viruses as divided into family and common species or genus:

| Family | Common Species or Genus |
|---|---|
| Herpesviridae | human herpes simplex virus types I & II |
| | bovine mammillitis virus |
| | herpes B virus of monkeys |
| | pseudorabies virus |
| | equine rhinopneumonitis virus |
| | varicella-zoster virus |
| | human cytomegaloviruses |
| | murine cytomegaloviruses |
| | Epstein-Barr virus |
| | Baboon herpes virus |
| | Chimpanzee herpes virus |
| | Marek's disease herpes virus |
| | Hinze virus |
| | Turkey herpes virus |
| | Herpes virus ateles |
| | Herpes virus saimiri |
| | Infectious bovine rhinotracheitis virus |
| Iridoviridae | African swine fever virus |
| | Frog virus group (Ranavirus) |
| | Iridovirus |
| | Chloriridovirus |
| Poxviridae | vaccinia virus |
| | smallpox virus |
| | cowpox virus |
| | monkeypox virus |
| | buffalopox virus |
| | camelpox virus |
| | ectromelia of mice virus |
| | rabbitpox virus |
| | Orf virus |
| | avipox virus |
| | sheep-pox virus |
| | goatpox virus |
| | lumpy skin disease (Neethling) virus |
| | myxoma virus of hares |
| | fibroma viruses of rabbits |
| | fibroma viruses of squirrels |
| | swinepox virus |
| | Yaba monkey virus |
| | molluscum contagiosum virus |
| Hepadnaviridae | human hepatitis B virus (HBV) |
| | woodchuck hepatitis virus |
| | ground squirrel hepatitis virus |
| | duck hepatitis virus |
| Orthomyxoviridae | Influenza virus, types A, B, and C |
| Paramyxoviridae | Newcastle disease virus of fowl |
| | human parainfluenza viruses |
| | Sendai virus |
| | mumps virus |
| | paramyxoviruses |

TABLE 1-continued

The following are enveloped viruses as divided into family and common species or genus:

| Family | Common Species or Genus |
|---|---|
| | measles virus |
| | rinderpest virus of cattle |
| | canine distemper virus |
| | peste-des-petits-ruminants virus of sheep and goats |
| | respiratory syncytial virus of man |
| | bovine respiratory syncytial virus |
| | pneumonia virus of mice |
| Rhabdoviridae | rabies virus |
| | vesicular stomatitis virus of: horses, cattle and swine |
| | chandipura virus |
| | lyssavirus |
| | duvenhage virus |
| | Lagos bat virus |
| | mokola virus |
| Bunyaviridae | bunyavirus (Bunyamwera, Bwamba, California, Capim, Guama, phlebovirus koongol, patois, simbu and tete viruses) |
| | sandfly fever virus |
| | Rift Valley fever virus of sheep and ruminants |
| | Nairovirus |
| | Crimean-Congo hemorrhagic fever viruses |
| | Uukuvirus |
| | Uukuniemi virus |
| | Hantaan virus |
| | Korean hemorrhagic fever virus |
| Filoviridae | ebola virus |
| | Marburg virus |
| Nodaviridae | Nodamura virus |
| Togaviridae | Alphaviruses |
| | aura virus |
| | Chikungunya virus |
| | eastern equine encephalitis virus |
| | getah virus |
| | mayaro virus |
| | middleburg virus |
| | mucamba virus |
| | ndumu virus |
| | O'Nyong-nyong virus |
| | pixuna virus |
| | ross river virus |
| | semliki forest virus |
| | sindbis virus |
| | una virus |
| | Venezuelan equine encephalitis virus |
| | western equine encephalitis virus |
| | Whataroa virus |
| | rubella virus |
| | mucosal disease virus |
| | border disease virus |
| | hog cholera virus |
| Flaviviridae | flavivirus |
| | Brazilian encephalitis virus |
| | Bussuquara virus |
| | dengue virus |
| | iiheus virus |
| | Israel turkey meningoencephalitis virus |
| | Japanese B encephalitis virus |
| | kunjin virus |

TABLE 1-continued

The following are enveloped viruses as divided into family and common species or genus:

| Family | Common Species or Genus |
|---|---|
| | Kyasanur forest disease virus |
| | langat virus |
| | louping ill virus |
| | modoc virus |
| | Murray valley encephalitis virus |
| | ntaya virus |
| | omsk hemorrhagic fever virus |
| | powassan virus |
| | St. Louis encephalitis virus |
| | spondwnei virus |
| | tick-borne encephalitis |
| | Uganda S virus |
| | US bat salivary gland virus |
| | wesselsbron virus |
| | west nile fever virus |
| | yellow fever virus |
| | zika virus |
| | European tick-borne encephalitis |
| | Far Eastern tick-borne encephalitis virus |
| | Russian tick-borne encephalitis |
| Retroviridae | type C oncovirus group |
| | type B oncovirus group |
| | type D retrovirus group |
| | avian complex leukemia virus |
| | Rous sarcoma virus |
| | murine complex leukemia virus |
| | mouse sarcoma virus |
| | murine mammary tumor virus |
| | feline leukemia complex virus |
| | feline sarcoma complex virus |
| | woolly monkey sarcoma virus |
| | gibbon leukemia virus |
| | Mason-Pfizer virus |
| | hamster leukemia virus |
| | rat leukemia virus |
| | bovine lymphoma virus |
| | human T cell leukemia viruses: types 1 and 2 etc. |
| | spumaviridae: syncytial and foamy viruses of humans, monkeys, cattle, cats |
| | visna virus of sheep |
| | Maedi virus |
| | progressive pneumonia viruses of sheep |
| | *human immunodeficiency viruses: (include HTLV III/LAV) HIV, HTLV IV, LAV-2, STLV-III$_{AGM}$ |
| Arenaviridae | Junin virus |
| | lassa virus |
| | machupo virus |
| | pichinde virus |
| | lymphocytic choriomeningitis virus |
| | lassa fever virus |
| | arenavirus |
| Other virus-like agents viroids-prions | kuru virus |
| | Creutzfeldt-Jakob disease virus |
| | scrapie virus |
| | transmissible mink encephalopathy |
| | Aleutian disease of mink |
| | bovine spongiform encephalopathy "virus" |

*NOTE: under Retroviridae
human T-lymphotropic virus type III (HTLV-III)
Lymphadenopathy virus (LAV)
human immunodeficiency virus (HIV)
simian T-lymphotropic virus type III (STLV-III$_{AGM}$)
human T-lymphotropic virus type IV (HTLV-IV)
(HTLV III and LAV are now usually referred to as HIV)

The term "tumor" as used herein includes both malignant and non-malignant neoplasms including tumors of viral, chemical, radiation, genetic and other origins. It can be of embryonic ectodermal origin, embryonic mesodermal origin, or embryonic endodermal origin. It can be from the embryonic surface ectoderm, the embryonic neuroectoderm, the embryonic head mesoderm, the embryonic paraxial mesoderm, the embryonic intermediate mesoderm, the embryonic lateral mesoderm, or the embryonic endoderm. Thus, tumors in an animal include: tumors of the skin and soft tissues; tumors of the muscle; tumors and tumor-like lesions of joints and adjacent soft tissues; tumors of bone and cartilage; tumors of the lymphoid and hematopoietic tissues; tumors of the respiratory system; tumors of the alimentary tract; tumors of the liver, gall bladder and pancreas; tumors of the urinary system; tumors of the genital systems; tumors of the mammary gland; tumors of the endocrine glands; and tumors of the nervous system and eye.

Human malignant tumors include: acute lymphoid leukemia; acute myeloid leukemia; chronic myeloid leukemia; chronic lymphoid leukemia; polycythemia vera; myelosclerosis with myeloid metaplasia; multiple myeloma; primary macroglobulinemia; Hodgkin's disease; non-Hodgkin's lymphoma; skin cancer; malignant melanoma; head and neck cancer; lung cancer; gastrointestinal cancer; breast cancer; gynecologic cancer; trophoblastic disease; testicular cancer; prostate cancer; renal carcinoma; bladder cancer; endocrine tumor; brain tumor; retinoblastoma; neuroblastoma; Wilm's tumor; osteogenic sarcoma; Ewing's sarcoma; and soft-tissue sarcoma.

The term "microorganism" as used herein includes parasites, bacteria, and other organisms and agents causing infestation. Parasites include arthropod parasites, helminth parasites, protozoal parasites, and hemaprotozoal parasites. Examples of these parasites include demodex mange, hookworm and coccidia.

The term "glycosylation" means the addition of carbohydrate molecules to a protein molecule. An acetylated mannan derivative, in particular acemannan, may exert its therapeutic effect by two possible mechanisms. One is the altering of glycosylation, such as inhibition of glucosidase I or the incorporation of the acetylated mannan derivative into glycoprotein. The other possible mechanism is enhancement of the antigenicity of the virus or the tumor, or the enhancement of immunocompetency of the hosts The enhancement of antigen can be achieved through the presentation by macrophage; reception by T or B cells or both, altered antigen presentation, or adjuvant effect. In a sense, acetylated mannan derivative enhances the recognition of a tumor or of an infectious agent, such as a virus or another microorganism, as "not self" by the host.

The administration of acetylated mannan derivative can be achieved by topical application, oral ingestion, IP route, IV route or other parenteral routes of administration.

Not only can the acetylated mannan derivative be given to the recipient as a single agent, it can also be used in combination with other known therapeutic agents that are characterized by their requirement of the participation or aid of the host's immune system to achieve their maximal therapeutic effect.

Acemannan has now been discovered to be a potent inducer of IL-I and prostaglandin E2 (PGE2) production by human peripheral blood adherent cells in culture. The instant invention is believed to be the first practical non-toxic stimulator of IL-1 release. IL-1 is an important macrophage product reported in the literature to influence the activity and production of lymphocytes, fibroblasts, B-lymphocytes and endothelial cells. See Old,. *Scientific American*, 258(5): 59–60, 69–75 (1988).

IL-1 induces fibroblast proliferation which is fundamental to wound healing. IL-1 also: (1) enhances bone marrow activity; it may be therapeutic in individuals whose bone-marrow is depressed; and (2) enhances the immune system in general.

A series of experiments with mixed lymphocyte cultures (MLC) has shown that acemannan increases the alloantigenic response of these lymphocytes in a dose-related fashion. Incubation of acemannan with monocytes permitted monocyte-driven signals to enhance the T lymphocyte response to lectin. Related studies on acemannan's effects on MLC have shown an increase in phagocytosis and activity of natural killer cells. Thus, in these in vitro test systems, acemannan is non-toxic and is an immunoenhancer.

Acemannan actively stimulates lymphocytes to secrete lymphokines and also causes HIV-infected lymphocytes to produce altered glycoproteins (GP-120) by a mechanism similar to that of glucosidase I inhibitors. See Gruters et al., *Nature* 330:74–77 (1987) and Pal et al., *Intervirol.* 30:27–35 (1989). Acemannan is phagocytized and apparently pumped to the Golgi/glycoprotein apparatus of the monocyte where it interferes directly with glycoprotein synthesis.

A. Toxicology

The toxicological effects of acemannan have been studied in both in vivo and in vitro systems. Acemannan is not mutagenic or blastogenic in in vitro test systems. In vitro, the compound was non-toxic for H-9, MT-2 and CEM-SS lymphoid cells. In vivo toxicology studies on acemannan include a 91-day subchronic oral toxicity study in dogs, a 180-day chronic oral toxicity study in rats and an 180-day chronic oral toxicity study in humans. In these studies, no toxic effects were noted in dogs receiving up to 825 mg/kg of acemannan per day for 91 days. No clinical, gross pathologic or toxic effects were noted in rats receiving up to 38,475 ppm acemannan in their feed for 180 days. No adverse clinical or toxic effects were noted in human patients receiving 800 mg per day of acemannan for 180 days.

In pilot studies, administration of acemannan to dogs caused an absolute monocytosis in blood samples taken for complete white blood cell counts and morphology differential. Within 2 hours after oral administration of high doses of acemannan, large activated monocytes appeared in circulation. A similar effect has been observed in humans.

A study was performed using human peripheral blood monocyte cell cultures and $^{14}$C-labeled acemannan to track the incorporation or absorption of acemannan into a biological system. In this study, detectable amounts of $^{14}$C-labeled acemannan were absorbed or ingested by human peripheral monocyte/macrophage cells. Peak incorporation occurred at 48 hours. At a concentration of 5 mg/ml, the $^{14}$C-labeled acemannan was not cytotoxic to the monocyte/macrophage cells, and the weight/volume (w/v) digested cell mass was 760 times greater than the w/v of the digested acemannan solution. These results suggest that the macrophage is capable of maintaining intracellular concentration of acemannan at very high levels that are not cytotoxic.

A pyrogen assay was performed in rabbits in accordance with the pyrogen test protocol outlined in the U.S.P. XXI, Biological Test [151], using a 1 mg/ml injectable solution of acemannan. More frequent temperature measurements were taken than specified in the U.S.P. because of the unknown systemic effects of injected acemannan. Temperature changes in test animals did not exceed minimum changes allowed by the U.S.P. protocol; therefore, the solution met the U.S.P. requirements for absence of pyrogens. Acemannan injectable elicited a maximum body temperature increase of 0.3° C. in one rabbit. This temperature rise occurred 90 minutes after injection. Acemannan is an inducer of IL-1 secretion by macrophages and monocytes in vitro. Since IL-1 is a potent pyrogen, this might explain the minimal, delayed temperature rise in this rabbit.

Twenty-four human subjects enrolled in and completed the study of the safety and tolerance of orally-administered acemannan. Clinical laboratory results showed that shifts out of the normal range occurred in the following: $CO_2$ in seven subjects, cholesterol in three subjects, triglycerides in two subjects, phosphorous in one, hemoglobin in four, basophils in two, monocytes in three, eosinophils in three, lymphocytes in four, neutrophils in two, and one each in red and white blood cells. Small numbers of red and white blood cells were also found in the urine. None of these shifts was clinically relevant.

Immune profile results showed group differences between Day 1 to Day 7 values for the following: CD-16, CD-4 (T-4), CD-8+Leu7, CD-4+CD-25, CD-8+CD-16, Leu7 and TQ-1. Mitogen responses were in the low range.

Vital signs did not appear to exceed normal ranges. There were no group differences in urine output. One subject in Group IV had diarrhea and loose stools during the study. One subject in Group I had loose stools during days 2 to 4 of the study. A total of 5 subjects reported a total of eight adverse events. All the events occurred in subjects receiving 1600 or 3200 mg oral acemannan daily for 6 days.

B. Mode of Administration

The physical properties of acemannan allow it to be formulated and incorporated into all pharmaceutical dosage forms known to those skilled in the art. The biopharmaceutical and toxicological properties of acemannan permit it to be used in tissues and organs of living organisms and to be administered over a wide range of doses.

Acemannan may be administered to an animal orally, parenterally, topically and locally, in a daily dosage of 0.001 mg/kg to 1000 mg/kg body weight per day.

Mixed with suitable auxiliaries, acemannan may be compressed or filled into solid dosage units such as pills, tablets and coated tablets, or it may be processed into capsules. These oral dose forms would be administered at a dosage of about 0.1 mg/kg to 1000 mg/kg of body weight per day.

By means of suitable liquid vehicles, acemannan can be injected in solutions, suspensions or emulsions. These products would be administered at a rate of 0.001 mg/kg to 1000 mg/kg of body weight per day. As an adjunctive component of a vaccine or other product, acemannan would be used at a rate of 0.001 to 1000 mg per unit dose of adjuvanted product.

Topical administration of acemannan can be in the form of a processed gel, cream, lotion, solution, ointment or powder. These formulations could contain up to 90% acemannan .

EXAMPLE 1

Production of Interleukin-1 and PGE2 by Human Adherent Peripheral Blood Leukocytes Stimulated with Acemannam Induction of IL-1 Production Human mononuclear cells were separated from heparinized whole blood by density-gradient centrifugation in Ficoll-Hypaque (Pharmacia, Sweden). After washing, cells were resuspended at a concentration of $2 \times 10^6$ cells/ml in RPMI-1640 with 25 mM Hepes, and supplemented with 50 U/ml penicillins, 50 µg/ml streptomycin and 2 mM L-glutamine. Two ml aliquots of the cell suspensions were dispensed into each well of a six-well plate and incubated for 1 hour at 37° C. in a 5% $CO_2$-humidified atmosphere. After removal of nonadherent cells, adherent cells were washed three times with the medium described above. Two ml of medium supplemented with 5% pooled human AB serum were added to each well. Cultures were stimulated with acemannan at different concentrations. Simultaneous controls with lipopolysaccharide (LPS) from *E. coli* (Sigma 0111:B4) at a final concentration of 20 μg/ml, and without any addition (background), were included. The cultures were incubated at 37° C. as described above for 24 hours. Supernatants were harvested, centrifuged to remove cells, and dialysed against 500 volumes of PBS for 48 hours (changed once), followed by 4 hours of dialysis against 20 volumes of RPMI-1640 with 25 mM Hepes, antibiotics and L-glutamine as described. Supernatants were frozen at $-20°$ C. until IL-1 activity was evaluated.

B. IL-1 Determination in Supernatants

Two different procedures were used to assay IL-1: (1) the thymocyte proliferation assay and (2) an ELISA assay specific for IL-1.

1. Tlymocytes from $C_3H/HeJ$ mice 5–8 weeks old were used. A homogeneous cell suspension was prepared in minimum essential medium (MEM) supplemented with 5% FCS, 100 U/ml penicillin, 50 g/ml streptomycin, 2 mM L-glutamine and $5 \times 10^{-5}$ M 2-mercaptoethanol, The cell concentration was adjusted and dispersed into 96-well plates at $1 \times 10^6$ cells/well. Phytohemagglutinin (PHA) was added to each well at a concentration of 10 μg/well. Samples were diluted serially and a volume of 25 μl was added to each well, starting from 1:10 to the final dilution. Every dilution was tested in quadruplicate. Plates were incubated at 37° C. in a humidified atmosphere with 5% $CO_2$ for 72 hours and were pulsed with [$^3$H]-thymidine (0.5 μg/well) during the last 16 hours. Cells were harvested onto fiberglass filters with an automatic cell harvester, and radioactivity was measured by standard scintillation procedures. Results are represented as cpm of thymidine incorporation by thymocytes in response to the supernatants at a final 1:10 dilution.

2. Two-site "Sandwich" ELISA for IL-1. This procedure has recently been described in *Journal of Immunology*, 138:4236 (1987), the disclosure of which is hereby specifically incorporated herein by reference. See also U.S. Pat. No. 3,654,090 and U.S. Pat. No. RE 31,006 to Schuurs et al. Briefly, monoclonal purified antibody IL-1-H6 against IL-1β, (100 μl/well, 10 μg/ml) was coated on vinyl assay plate wells overnight at 4° C. The wells were washed with PBS/0.5% Thimerosal and countercoated with 200 μl of 5% non-fat dry milk/0.5% Thimerosal/PBS for 1 hour at room temperature. After washing, 50 μl/well of sample or human recombinant IL-1 standard and 50 μl of another monoclonal antibody against a non-overlapping epitope of IL-1, [biotinylated IL-1β-H67 (2 μg/ml) in 1% non-fat dry milk/ 0.5% Thimerosal/PBS], were added, and the plates were incubated for 2 hours at room temperature. After washing, 100 μl/well of a 1:1000 dilution of streptavidin-peroxidase were added and the plate was incubated for 1 hour. The wells were washed, incubated for 30 minutes in the dark with 100 μl OPD substrate solution, and absorbance at 450 nm was measured.

C. Determination of PGE2

$PGE_2$ was evaluated with a radioimmunoassay in the same non-dialyzed supernatants. The antibody to $PGE_2$ (ICN Biomedical, Inc., Costa Mesa, Calif.) was used according to the manufacturer's instructions, which are incorporated herein by reference.

D. Observations

Representative experiments are shown in Table 2. Acemannan is a potent inducer of IL-1 production by human adherent peripheral blood leukocytes. At doses between 1 and 10 μg/ml, acemannan extract induced production of IL-1 comparable to that induced by 20 μg/ml LPS, which is the reference inducer of IL-1 production. Acemannan in the same dose range also induced the production of $PGE_2$ at levels comparable to those induced by 20 μg/ml LPS (positive control).

TABLE 2

INDUCTION OF $PGE_2$ SYNTHESIS BY HUMAN PERIPHERAL BLOOD ADHERENT CELLS STIMULATED BY ACEMANNAN AND BY LIPOPOLYSACCHARIDE (LPS).

| Experiment Number | Stimulator | PGE2 (ng/ml) |
| --- | --- | --- |
| 198 | 0 | 0 |
|  | LPS 20 μg/ml | 2.6, 3.9 |
|  | Acemannan 10 μg/ml | 3.5 |
|  | Acemannan 1 μg/ml | 0 |
| 148 | 0 | 0 |
|  | LPS 20 μg/ml | 0.5, 1.3 |
|  | Acemannan 10 μg/ml | 0.7 |

EXAMPLE 2

Effect of Acemannan on Phagocytosis In Vitro

The effect of acemannan was studied in vitro to ascertain its effect on phagocytic function. CBA mice were injected IP with 1 mg/kg acemannan, and peritoneal and splenic macrophages were collected 3 days later. Thioglycolate and saline were similarly tested as positive and negative controls, respectively. The macrophages were incubated with sheep red blood cells (SRBC) as ingestion particles in the presence and absence of anti-SRBC titers, and phagocytosis was measured histologically as percent cells that ingested SRBC. Although non-specific phagocytosis was increased slightly after acemannan treatment, phagocytosis was significantly increased in the presence of antibody. In the presence of complement, acemannan-stimulated, antibody-mediated phagocytosis was increased to an even greater extent. These results indicate that acemannan may increase the number of macrophages and enhance their phagocytic activity. Such responses may contribute to acemannan's effectiveness as a stimulant of wound healing and as an anti-infectious agent.

A. Methods and Materials

Acemannan was stored at room temperature in its dried form. The amount needed for each experiment was weighed out and microwaved in 2-minute exposures at 600 watts of power. It was then transferred to a sterile plastic centrifuge tube and microwaved for 1 additional minute. The material was diluted in cell culture medium (RPMI-1640) to the desired concentration.

Phagocytic Cells: Mouse spleen cells were obtained from BALB/c mice purchased from Harlan Sprague-Dawley. The mice were killed by $CO_2$ asphyxiation, and their spleens were removed aseptically. Subsequently, the cells were separated into adherent and non-adherent populations by nylon wool column fractionation according to the method of *Journal of Immunology*, 71:220, the disclosure of which is hereby specifically incorporated by reference. Adherent cells were determined by microscopic analysis, as described below, to be macrophages (monocytes) and lymphocytes in a ratio of 4 to 1. After single-cell suspensions were obtained by monolayer disruption, both adherent and non-adherent single cell preparations were placed on ficoll-hypaque and centrifuged to obtain a mixture of lymphocytes and macrophages.

Blastogenesis Assay: A standard blastogenesis assay was set up as outlined below. The mitogen used in the assay was PHA-P obtained from Burroughs Wellcome. As indicated for individual experiments, the cultures were maintained for 72 hours in a 5% $CO_2$, humidified atmosphere. Tritiated thymidine was added during the last 6 hours of the culture. Cell concentrations per well, using flat bottom microtiter tissue culture plates, were $5 \times 10^5$ mouse cells/0.2 ml. Cells were deposited in the wells and acemannan or mitogen was added. A stimulation index (SI) was calculated using the formula:

$$SI = \frac{cpm \text{ experimental} - cpm \text{ background}}{cpm \text{ control} - cpm \text{ background}}$$

Cell Staining: Briefly, smears of cells were stained by non-specific esterase stain as follows. Approximately $2 \times 10^6$ cells in 2 drops were mixed with 2 drops of fetal calf serum and 4 drops of a fixative solution consisting of a mixture of 25 ml of 35% formaldehyde, 45 ml of acetone, 100 mg of $KH_2PO_4$, 10 mg of $Na_2HPO_4$ and 30 ml of water. The slides were incubated with a mixture of 10 mg of naphthyl acetate and 4.5 mg of Fast Blue stain in 1.4 ml of ethylene glycol monomethyl ether with 5 ml of 0.1M Trismaleate buffer, pH 7.8 (Wright's stain). The stain was allowed to react for 10 minutes, then washed in water for 20 seconds. A counterstain of 0.2 g of Giemsa stain, 12.5 ml of ethanol and 12.5 ml of glycerol was used for 30 seconds before. washing again.

Induction of Peritoneal Macrophage Cells: Saline thioglycolate broth (1 mg/kg) or acemannan (1 mg/kg) was injected IP into female BALB/c mice to induce peritoneal exudate macrophage cells. Induced cells were removed from the peritoneal cavity 3 days post-injection.

Macrophages were washed twice with phosphate-buffered saline (PBS) and covered with 2 ml of fresh medium; 0.1 ml of the macrophage suspension was added to each tube. Cultures were placed for 30 to 60 minutes into a 37° C., humidified 5% $CO_2$-95% air incubator. Cultures were washed twice with PBS and covered with 2 ml of PBS. One of each pair of coverslips was removed with needle-nosed forceps, dipped for 5 seconds only in distilled water, and promptly replaced in the culture dish. The PBS was removed, and the cultures were covered with ice-cold glutaraldehyde. After 10 minutes, the glutaraldehyde was removed, and the coverslips were overlaid with distilled water.

Mounted coverslips were examined promptly with the oil immersion lens of a phase contrast microscope. Attachment was scored on the coverslip that was not subjected to hypotonic shock, whereas ingestion was scored on the coverslip that was lysed in distilled water.

Antibody-Dependent and Antibody-Independent Phagocytosis: SRBC, obtained from Austin Biologics Laboratory, Austin, Tex., were washed three times in PBS (pH 7.2). BALB/c mice were given IP injections of $10^6$ cells and bled on day 14 post-injection. Serum was collected, pooled and heat inactivated at 56° C. for 45 minutes. Agglutination titers were determined to be 1024 using round-bottomed microtiter wells.

Antibody-independent phagocytosis was determined by incubation of SRBC (0.5% v/v) with macrophages ($10^6$) in RPMI-1640 containing 20% fetal calf serum (FCS). Slides were prepared at various intervals and stained. The percent macrophages that had ingested red cells was determined visually by counting 200 cells/slide and three slides/animal.

Antibody-dependent phagocytosis was determined using SRBC (0.5% in RPMI-1640 with 20% FCS) mixed with anti-SRBC serum or IgM fraction (minimum titer of 2000). The mixture was incubated for 15 minutes at 37° C., then washed twice in PBS (pH 7.2) and resuspended to the original volume.

Serum Fractionation: Whole serum was fractionated to remove IgM by euglobulin precipitation and dialysis against distilled water. After dialysis at 4° C. for 24 hours, precipitate was removed by centrifugation at 1500×G for 20 minutes, and supernatant was analyzed by ion electrophoresis and complement-mediated lysis. Less than 5% of the original IgM remained.

B. Results

To evaluate the effect of acemannan on macrophages, the first experiment utilized mouse spleen cells cultured in vitro with acemannan (Table 3).

TABLE 3

PERCENT CELL TYPES BY HISTOLOGICAL EVALUATION OF MOUSE SPLEEN CELLS IN CULTURE

| Time in | | Acemannan (µg/well) | | | |
|---|---|---|---|---|---|
| Culture | Cells(a) | 0.0 | 0.002 | 0.02 | 0.2 |
| 72 hours | macrophages | 30 ± 6 | 32 ± 7 | 41 ± 3 | 45 ± 9 |
| | lymphocytes | 70 ± 5 | 68 ± 8 | 59 ± 3 | 55 ± 6 |
| 96 hours | macrophages | 22 ± 4 | 28 ± 4 | 36 ± 6 | 38 ± 8 |
| | lymphocytes | 78 ± 8 | 72 ± 7 | 64 ± 10 | 62 ± 4 |

(a) Macrophages (monocytes) were determined by esterase staining. The results are expressed as mean ± S.D. The results are from six experiments with 200 cells studied/experiment. "Lymphocytes" are cells that did not stain by esterase and had the appearance of lymphocytes by Wright's stain.

Cultures were incubated for 72 or 96 hours, and at termination of the experiment smears were made and stained by Wright's stain and by the esterase method. The relative percentage of macrophages and lymphocytes was determined. At 72 hours there was a dose-related increase in macrophage numbers from 30% with no acemannan to 45% with 0.2 µg of acemannan per well. Since data are expressed as percent cells, there was a concomitant reduction in lymphocytes. At 96 hours there was also a dose-related increase in the percentage of macrophages in the presence of acemannan. At 96 hours, the cultures with 0.2 µg of acemannan per well showed significant acidosis, as indicated by a yellow coloring.

Furthermore, 96-hour cultures had a lower percentage of macrophages, possibly due to the longer time in culture. To relate the acemannan-induced increase in macrophage numbers to a known standard, a similar experiment was conducted with the mitogen PHA-P. Results are shown in Table 4.

TABLE 4

PERCENT CELL TYPES BY HISTOLOGICAL EVALUATION OF MOUSE SPLEEN CELLS IN CULTURE

| Time in | | PHA-P (µg/well) | | | |
|---|---|---|---|---|---|
| Culture | Cells(a) | 0.0 | 0.02 | 0.01 | 0.2 |
| 72 hours | macrophages | 33 ± 8 | 32 ± 6 | 30 ± 6 | 31 ± 5 |
| | lymphocytes | 70 ± 12 | 68 ± 8 | 70 ± 6 | 69 ± 4 |
| 96 hours | macrophages | 18 ± 6 | 21 ± 3 | 26 ± 6 | 25 ± 5 |
| | lymphocytes | 77 ± 10 | 79 ± 4 | 74 ± 8 | 75 ± 6 |

(a) Monocytes were determined by esterase staining. The results are expressed as mean ± S.D. The results are from six experiments. "Lymphocytes" are cells that did not stain by esterase and had the appearance of lymphocytes by Wright's stain.

Although the percentage of macrophages did not change at 72 hours, there was a dose-related increase in macrophages after incubation with PHA-P for 96 hours. By comparison, acemannan was twice as effective as PHA-P. The percentage of macrophages increased a maximum of 16 with acemannan compared to 7 with PHA-P (Tables 3 and 4).

Since acemannan appeared to increase the percentage of macrophages, it was decided to determine whether the activity of the phagocytes was also increased. Peritoneal exudate cells from CBA mice given saline, thioglycolate broth or acemannan were used [as phagocytes] with sheep red blood cells as the particles to be ingested (Table 5).

TABLE 5

NONSPECIFIC PHAGOCYTOSIS OF SHEEP ERYTHROCYTES BY PERITONEAL EXUDATE(a)

| | Percent of Phagocytosis(b) Time (minutes) | | | | | |
|---|---|---|---|---|---|---|
| Trmt. | 0 | 5 | 10 | 20 | 60 | 120 |
| Saline | 3 ± 3 | 11 ± 6 | 15 ± 10 | 25 ± 9 | 45 ± 12 | 52 ± 15 |
| Thio. | 1 ± 1 | 14 ± 8 | 20 ± 8 | 52 ± 14(c) | 84 ± 32(c) | 89 ± 21(c) |
| Ace. | 3 ± 2 | 10 ± 6 | 12 ± 8 | 41 ± 18 | 61 ± 18 | 63 ± 23 |

(a) The results were determined by counting 200 cells/slide with two slides/animal. The results are based on two experiments.
(b) Percent phagocytosis indicates the proportion of cells showing erythrocyte ingestion. The results are expressed as mean ± S.D.
(c) Significantly different from saline control group, assessed by the Student's t-test at the 95% confidence level.

Over a 120-minute period, nonspecific phagocytosis increased from 3% to 52% in saline controls, whereas percent phagocytosis in cells from thioglycolate broth-treated animals rose to 89%. Phagocytosis in acemannan-treated animals rose to 63% at 120 minutes. Acemannan-stimulated phagocytosis was greater than that in controls after 20–120 minutes; however, the differences were not statistically significant.

To determine whether the acemannan effect on phagocytosis was antibody-dependent, a similar experiment was performed with anti-SRBC (Table 6).

TABLE 6

ANTIBODY MEDIATED PHAGOCYTOSIS(a)

| Phagocyte | | Antibody Titer (x 103)(b) | | | |
|---|---|---|---|---|---|
| Source | Pretreatment | 0 | 2 | 4 | 8 |
| Peritoneum | Saline | 15 ± 8 | 43 ± 10 | 39 ± 9 | 19 ± 11 |
| | Thioglycolate | 49 ± 11 | 89 ± 22 | 80 ± 22 | 58 ± 14 |
| | Acemannan | 36 ± 14 | 73 ± 13(c) | 62 ± 8 | 40 ± 13 |
| Spleen | Saline | 11 ± 4 | 38 ± 9 | 32 ± 11 | 20 ± 4 |
| | Thioglycolate | 29 ± 9 | 73 ± 13 | 54 ± 16 | 38 ± 12 |
| | Acemannan | 21 ± 10 | 60 ± 9(c) | 51 ± 17 | 26 ± 11 |

(a) Phagocytosis is expressed as the mean % of cells showing erythrocyte ingestion ± S.D.
(b) The antibody titer by agglutination was shown to be 1:1024. Pre-treatment and cell sources are discussed in Methods.
(c) Significantly different from saline control, assessed by the Student's t-test at the 95% confidence level.

Sera were inactivated with heat (56° C. for 30 minutes), and the antibody titer used was $2 \times 10^3$, well above the hemagglutination titer. In this experiment, macrophages were obtained from two sources, the peritoneal cavity and the spleen. Again, mice were pretreated with IP injections of 1 ml of 0.9% saline, 1 mg/kg thioglycolate or 1 mg/kg acemannan. At a titer of $2 \times 10^3$, the phagocytic activity of thioglycolate-induced peritoneal macrophages was twice as great (89% vs. 43%) as activity from the saline-induced controls, whereas acemannan-induced macrophages were more active by 30% (73% vs. 43%) compared to controls. The difference between phagocytic activity in the acemannan-treated and saline control groups was statistically significant.

Similar results were seen with macrophages obtained from mouse spleens. Phagocytic activity was lower than that of macrophages obtained from the peritoneal cavity, possibly due to manipulations of the spleen cells. Again, at a titer of $2 \times 10^3$, acemannan-induced macrophages were significantly higher in phagocytic activity than saline controls at the 95% confidence level; phagocytic activity was similar to control at a titer of $8 \times 10^3$.

To determine the effect of complement (C') on antibody-mediated phagocytosis, an experiment utilizing addition of C' to media was undertaken. (Table 7).

TABLE 7

COMPARISON OF COMPLEMENT-MEDIATED PHAGOCYTOSIS

| | | % Phagocytosis(a) | |
|---|---|---|---|
| Cell Source | Phagocyte Inducer | +C' | –C' |
| Peritoneum | Saline | 24 ± 11 | 18 ± 9 |
| | Thioglycolate | 84 ± 10 | 62 ± 12 |
| | Acemannan | 70 ± 8(b) | 54 ± 4 |
| Spleen | Saline | 18 ± 11 | 16 ± 9 |
| | Thioglycolate | 54 ± 9 | 41 ± 11 |
| | Acemannan | 48 ± 10 | 35 ± 6 |

(a) Phagocytosis is measured as percent uptake of sheep erythrocytes ± S.D. after incubation for 30 minutes. Guinea pig complement was added.
(b) Significantly different compared to –C', assessed by the Student's t-test at the 95% confidence level.

To assure that lysis would not occur, IgM-depleted mouse serum was used (see Methods). The titer utilized was 3000, as determined by hemagglutination and the Coombs technique. Cells from both the peritoneal cavity and spleen were more active in phagocytosis with the addition of C' than without C', although the difference was statistically significant only with peritoneal cells induced by acemannan.

Finally, an experiment was performed to differentiate the effect of acemannan phagocytosis and adherence (Table 8).

TABLE 8

COMPARISON OF PHAGOCYTOSIS AND ADHERENCE(a)

| Cell Source(b) | Pre-treatment | Phagocytosis | Adherence |
|---|---|---|---|
| Peritoneum | Saline | 5 ± 8 | 6 ± 4 |
| | Thioglycolate | 12 ± 9 | 23 ± 9(c) |
| | Acemannan | 11 ± 9 | 18 ± 10(c) |
| Spleen | Saline | 8 ± 7 | 14 ± 11 |
| | Thioglycolate | 14 ± 6 | 36 ± 10(c) |
| | Acemannan | 10 ± 8 | 20 ± 7(c) |

(a) Cell mixtures were allowed to incubate for 7 minutes.
(b) Results are reported as percent phagocytes showing phagocytosis or adherence ± S.D. The results are from one experiment with 200 cells scored/animal with three animals used.
(c) Significantly different from saline controls, assessed by the Student's t-test at the 95% confidence level.

In this experiment, antibody to SRBC was used in a titer of 2,000, but the experiment was stopped after 7 minutes. Acemannan-induced macrophages from both the peritoneum and spleen were more efficient in adherence than the saline controls and, as seen previously, less efficient than the thioglycolate-induced group.

C. Discussion

The results indicate that acemannan both directly and indirectly stimulates phagocytosis. The results also indicate that acemannan enhances phagocytosis by macrophages, both non-specifically and specifically, through antibody-mediated reactions. This demonstrates that acemannan has immunostimulatory properties on phagocytes.

EXAMPLE 3

The Effects of Acemannan on Nonspecific Tumor Lysis

This example investigates the possibility of nonspecific tumor death induced by acemannan-stimulated phagocytes.

A. Procedures

Acemannan Polymer: Acemannan was kept in a dried form. The amount needed for each experiment was weighed and microwaved in 2-minute exposures at 600 watts of power. The material was transferred to a sterile centrifuge tube (15 ml) and microwaved for one additional minute. The material was diluted in Hanks Balanced Salt Solution (HBSS) to the concentration needed. In some experiments, material was sterilized by autoclaving, with no apparent loss in activity.

Cells: Macrophages were harvested from the peritoneal cavity of BALB/c female mice obtained from Harlan/Sprague Dawley. Either thioglycolate broth (25 mg/kg) or acemannan (25 mg/kg) was injected IP into some groups of animals 6 days before harvesting. Saline stimulated cells were also utilized as an additional control. Harvested cells were washed three times in HBSS and diluted in RPMI-1640 to a concentration of $5 \times 10^6$/cells/ml.

Target cells: Target cells were obtained from the American Type Culture Collection (C3H/HeN Fibrosarcoma L929) and maintained in passage. Labeling was done with 150 mCi of $^{51}$Cr mixed with 1 ml of the cell suspension containing $10^7$ cells in RPMI-1640. Cells were incubated for 1 hour, washed with RPMI-1640 three times and adjusted to a final concentration of $5 \times 10^4$ cells/ml.

B. Assay

Aliquots of effector cells (100 cells/$\mu$l) were placed in flat-bottomed microtiter plates. $^{51}$Cr-labeled cells were added with a minimum of three replicates per experimental point. Test plates were incubated at 37° C. in 7% $CO_2$ (previously 5% $CO_2$) for 20 hours. Supernatants (100 $\mu$l), were obtained after centrifugation of the plates at 250×G for 15 minutes. The amount of radioactivity was assayed on a Packard gamma counter. Controls consisted of thymocytes. The percent of cytotoxicity (% CT) was determined by:

$$\% \, CT = \frac{cpm \text{ in test cells} - cpm \text{ in control cells } CT}{\text{total } cpm \text{ of target cells}}$$

C. Results

Table 9 shows the results of the initial experiments.

TABLE 9

EFFECT OF ACEMANNAN ON CYTOTOXICITY

| Cells | cpm ± S.D.(a) | percent cytotoxicity |
|---|---|---|
| thioglycolate stimulated in vivo | 2,800 ± 300 | 6.6 |
| thioglycolate stimulated in vitro | 2,950 ± 260 | 7.0 |
| nonstimulated | 2,870 ± 400 | 6.8 |
| Acemannan-stimulated in vivo | 3,100 ± 360 | 7.4 |

TABLE 9-continued

EFFECT OF ACEMANNAN ON CYTOTOXICITY

| Cells | cpm ± S.D.(a) | percent cytotoxicity |
|---|---|---|
| Acemannan-stimulated in vitro | 21,000 ± 900 | 50.0 |
| Acemannan-stimulated in vivo and in vitro | 20,500 ± 1100 | 48.8 |

(a) total cpm of target cell = 42,000

Thioglycolate-stimulated macrophages incubated with $^{51}$Cr target cells released $^{51}$Cr at an average of 2800 cpm, whereas acemannan-labeled cells released radioactivity at an average of 3100 cpm. There was no statistical difference between these groups. Nonstimulated macrophages released in the range of 2800 cpm. However, macrophages stimulated with acemannan in vitro had a 51Cr release of 21,000 cpm. This indicates two things: 1) acemannan does not induce a long standing cytolytic effect, and 2) its activation can occur in a relatively short time in tissue culture. The percent cytotoxicity is parallel to the cpm released from target cells when destroyed.

A subsequent experiment using the cytotoxic assay over time is shown Table 10.

TABLE 10

TIME DEPENDENT EFFECT OF ACEMANNAN ON CYTOTOXICITY

| Time(a) | Stimulation | cpm(b) | Percent Cytotoxicity |
|---|---|---|---|
| 0 | Acemannan | 800 | 2.0 |
|   | Thioglycolate | 780 | 1.9 |
| 3 | Acemannan | 1,400 | 3.5 |
|   | Thioglycolate | 800 | 2.0 |
| 6 | Acemannan | 18,000 | 46.0 |
|   | Thioglycolate | 1,200 | 3.0 |
| 9 | Acemannan | 22,600 | 57.9 |
|   | Thioglycolate | 2,200 | 5.8 |
| 12 | Acemannan | 22,500 | 57.6 |
|   | Thioglycolate | 2,300 | 5.8 |
| 15 | Acemannan | 23,000 | 58.9 |
|   | Thioglycolate | 21,100 | 5.8 |

(a) Time in hours after injection
(b) Cpm control cells = 39,000

The cytotoxic effect of acemannan began within 6 hours after stimulation and increased to its maximum by 9 hours. The mechanism of this activation has not been investigated.

The data shown in this example indicate that acemannan may have an important role in the nonspecific therapy of cancer.

Screening of Acemannan for Potential Efficacy Against Equine Sarcoid. Three sarcoids on two horses were treated both parenterally and intralesionally with acemannan. The goals of this trial were to determine whether acemannan might be an effective treatment against equine sarcoid and also to observe the horses for adverse reactions. On horse 1, one sarcoid completely resolved while a second sarcoid did not decrease in size. A third nodular sarcoid developed during treatment. On horse 2, a single sarcoid completely resolved. These results suggest that acemannan may be useful in the treatment of equine sarcoid.

Two horses with three suspicious lesions were purchased at a sale. The lesions were photographed, measured and confirmed by histopathology as sarcoids.

Horse 1: Day 1. Each of the two lesions on the right rear leg was treated by direct injection (20-ga. needle), with 50 mg acemannan diluted in 10 ml saline (lesion 1) and 5 ml saline (lesion 2). Twenty-five mg acemannan diluted in 7.5 ml saline was also given IV.

Day 7. Lesion 1 (upper lesion) was treated (18 ga. needle) with 50 mg acemannan diluted in 10 ml saline. Lesion 2 was treated with 25 mg diluted in 7.5 ml saline. Fifty mg in 10 ml saline was given IV.

Day 14. Lesion 1 was treated with 50 mg in 10 ml saline, whereas lesion 2 was treated with 25 mg in 5 ml saline. Seventy-five mg in 25 ml saline was given IV.

Day 21. Lesion 1 was treated with 50 mg in 10 ml saline, and lesion 2 was treated with 25 mg in 10 ml saline. One hundred mg in 25 ml saline was injected IV.

Day 29. Lesion 1 was treated as on day 21, but because of local swelling lesion 2 was not treated directly. One hundred mg in 25 ml saline was given IV.

Day 42. Lesion 1 was not treated directly. Lesion 2 was treated with 25 mg in 10 ml saline. One hundred mg in 50 ml saline was given IV.

Day 57. Horse 1 was euthanized. Tissue samples were taken at the site of lesion 1 and from lesion 2, inguinal lymph nodes and a nodular lesion on his left shoulder that had developed during the course of treatment.

Horse 2: Day 1. The lesion on the lower left thorax was treated with 50 mg acemannan diluted in 30 ml saline. One half was injected subcutaneously (S/Q) and the other half intralesionally.

On days 6, 16, 24, 30, 49, 56, 63, 70 and 77 horse 2 was given 100 mg acemannan IV diluted in 60–120 ml saline, the amount of diluent varying as required to make a clear solution.

On days 105, 113 and 120, the lesion was treated with mg acemannan diluted in 5 ml saline, intralesionally and S/Q at the base of the lesion. An additional 75 mg was given IV.

Results-Horse 1: Day 1. Lesion 1 measured 2.5 cm (length horizontally)×2.5 cm (height vertically)×1 cm (thickness). The resolution of this lesion can be followed below:

| Horse 1 - Lesion 1 | |
|---|---|
| Day | Measurements |
| 1 | 2.5 cm × 2.5 cm × 1 cm |
| 7 | 2.5 cm × 1.75 cm × 1 cm |
| 14 | 2.0 cm × 1 cm × 1 cm |
| 21 | 2.0 cm × 1 cm × now flush with skin level |
| 29 | 2.0 cm × 1 cm × flat and dry |
| 42 | all but healed |
| 54 | completely healed |

Lesion 2 measured 2 cm×2 cm×1 cm on Day 1 and never changed significantly.

| Horse 1 - Lesion 2 | |
|---|---|
| Day | Measurements |
| 1 | 2 cm × 2 cm × 1 cm |
| 7 | 2 cm × 2 cm × 1 cm |
| 14 | 2 cm × 2 cm × 1 cm |
| 21 | 2 cm × 2 cm × 1 cm |
| 29 | 2 cm × 2 cm × 1 cm - entire hock still swollen and painful |
| 42 | size slightly less - still swollen, not as painful |
| 54 | same size - hock swelling down 65% |

Results-Horse 2: Day 1. The lesion measured 5 cm×3.5 cm×2.5 cm with a pedunculated base of 2.5 cm. The changes until complete resolution are shown below:

| Horse 2 - Lesion 1 | |
|---|---|
| Day | Measurements |
| 1 | 5 cm × 3.5 cm × 2.5 cm |
| 6 | no change |
| 16 | no change - more granulomatous |
| 24 | 5 cm × 3 cm × 2.5 cm |
| 30 | less granulomatous |
| 49 | 4 cm × 3 cm × 2 cm |
| 56 | 4 cm × 3 cm × 2 cm |
| 63 | 3.8 cm × 3 cm × 2 cm |
| 70 | 3.7 cm × 2.6 cm × 1.8 cm |
| 77 | 2.7 cm × 2 cm × 1.3 cm |
| 105 | 2.5 cm × 2 cm × 1.3 cm |
| 113 | 3.5 cm × 2.25 cm × 1.5 cm |
| 120 | 2.5 cm × 2.4 cm × 0.6 cm |
| 177 | Lesion completely resolved |

After IV administration to these horses, there were no changes in heart rate, no sweating, muscle fasciculation or obvious signs of distress. A slight increase in depth of respiration was noted in horse 1 only. Locally, horse 1 showed an inflammatory cellulitis of a mild nature at lesion 1 and of an acute painful type at lesion 2, enough so that the lesion was not injected as scheduled on day 29. Lesion 2 was more fibrous and much more difficult to inject, so that there was more leakage S/Q. This could account for the lack of effect on lesion 2. Horse 2 did not show cellulitis.

The fact that a nodular sarcoid developed during the course of treatment leads one to suspect that the main effect of acemannan is a local tissue reaction rather than a systemic one, although IV administration may sensitize the sarcoid to intralesional treatment.

The exact date at which the lesion on horse 2 resolved is unknown because the investigator was on a 60-day sick leave between day 113 and day 177. Judging from the lack of significant reduction in tumor size by day 56, it would appear that weekly IV administration alone had little effect on the sarcoid on horse 2.

EXAMPLE 4

Enhancement of Allo-Responsiveness of Human Lymphocytes by Acemannan

This example was designed to test the capacity of acemannan to enhance immune response to alloantigen and to test whether the potential enhancement is a monocyte-driven phenomenon. Acemannan did not enhance lymphocyte response to syngeneic antigens in the mixed lymphocyte culture (MLC), but, importantly, it increased alloantigenic response in a dose-response fashion ($2.6 \times 10^{-7}$–$2.6 \times 10^{-9}$M). This effect of acemannan was shown to be a specific response and to concur with concentrations of in vitro acemannan achievable in vivo. A separate series of mixing experiments demonstrated that acemannan incubation with monocytes permitted monocyte-driven signals to enhance T cell response to lectin. It is concluded that acemannan is the active ingredient of the Aloe vera plant and is an important immunoenhancer in that it increased lymphocyte response to alloantigen. It is suggested that the mechanism involves enhancement of monocyte release of IL-1 under the aegis of alloantigen. This mechanism may explain in part the capacity of acemannan to abrogate viral infections in experimental animals and man.

This example was designed to directly assess the impact of acemannan as an immune enhancer in the model of monocyte-T-lymphocyte, cell-cell interaction response to alloantigen presented in the mixed lymphocyte culture. This model tests the capacity of acemannan to stimulate additional monocyte-macrophage functions in an immunologically relevant model.

A. Materials and Methods

1. Cell Preparation. Mononuclear leukocytes were obtained from the peripheral blood of normal, informed and consenting human volunteers under the aegis of a study approved by the Institutional Review Board of the University of Texas Southwestern Medical Center at Dallas. Peripheral blood was diluted 1:3 in Hanks' balanced salt solution (HBSS) and layered on top of a ficoll-hypaque gradient. Cells from subjects known to be major histocompatibility disparate were obtained on each study day to ensure a positive mixed lymphocyte reaction. For specific experiments, more carefully characterized pedigrees of cells which inhibit the mononuclear leukocyte pool were isolated. T-lymphocytes were isolated by the standard nylon wool separation technique. The nylon effluent cells contained about 90% pure T cells. T-8 lymphocytes and monocyte-macrophages preferentially adhere to the column. The adherent population was removed by forcibly pushing media through the column with a plunger. To enrich for monocytes (macrophages), the glass adherence procedure was utilized to produce a population greater than 95% pure.

2. Acemann an. Acemannan was tested in these studies by preparing a 0.5% (w/v) solution in RPMI-1640 medium and further diluting to the following working concentrations:

$2.6\times10^{-7}M$, $2.6\times10^{-8}M$ and $2.6\times10^{-9}M$.

3. Mixed Lymphocyte Cultures (MLC). Unidirectional MLC were set up in microtiter, flat-bottom tissue culture plates (Costar Co., Cambridge, Mass.). Mononuclear cells, isolated by the ficoll-hypaque density gradient technique discussed above, served as stimulator cells after exposure to 2000 rads for 30 minutes in a cesium source (Gammacell, Atomic Energy of Canada, Ontario, Canada). Responder cells that had been similarly isolated and stimulators were adjusted to $1.3\times10^6$ cells/ml. To each well the following were added: 25 $\mu l$ of acemannan or media (control), 25 $\mu l$ of RPMI-1640 supplemented with 10% fetal bovine serum and 75 $\mu l$ of each cell population. Cells were incubated at 37° C. in 5% $CO_2$: 95% air for 6 days. Cultures were pulsed with 25 $\mu l$ of $^3H$-thymidine (1 $\mu Ci$/well) for 4 hours, after which the cells were harvested and counted. To test the specificity of acemannan on the afferent recognition and response to MLC, additional unidirectional MLC were set up with the agent added just 20 minutes before the cells were pulsed with $^3H$-thymidine.

4. Monocyte-T Cell Interaction. Lewis female rat spleens were teased through a sterile steel mesh into RPMI-1640 medium. Mononuclear leukocytes were collected from the interface of a ficoll-hypaque density gradient as described above. Monocytes, obtained by enrichment on glass petri dishes and adjusted to a final concentration of $10^6$/ml, were incubated with varying doses of acemannan or medium (control) in a total volume of 2 ml and incubated for 24 hours at 37° C. The monocytes were harvested, extensively washed with fresh medium and co-cultured with syngeneic T lymphocytes at a ratio of 10 T-cells:1 monocyte, with the plant lectin phytohemagglutinin (Difco, Detroit, Mich.) (1:100) for 48 hours at 37° C. Cells were harvested over a MASH II (Whittaker, MA Bioproducts, Walkersville, Md.), placed in fluor and counted in a scintillation counter (Beckman Laboratories, Chicago, Ill.). A control experiment was performed by incubating T lymphocytes with acemannan, followed by wash and co-culture with freshly prepared T lymphocytes, again at 10:1 along with PHA-P.

B. Results

1. Alloantigenic Response. Acemannan had no statistically important effects on the response of T-cells to autoantigens. When the agent was added at the beginning of MLC, cells receiving syngeneic stimulation incorporated tritiated thymidine equally in the presence or absence of test reagent at the doses described. In the absence of oral acemannan these MLC incorporated $2616\pm1099$ cpm of tritiated thymidine at the end of a 4 hour pulse. Although there was a trend upward with respect to the dose of agent added ($3281\pm1355$ at $2.6\times10^{-9}M$, $3742\pm1670$ at $2.6\times10^{-8}M$, and $3828\pm1978$ at $2.6\times10^{-7}M$), none of these rates of isotopic incorporation into DNA was different to a statistically significant degree.

In contrast to the absence of effect of acemannan on autoresponse in the MLC was the agent's effect on alloresponse in the same immunologic assay. First, acemannan did not interfere with the capacity of lymphocytes to recognize and respond to class II alloantigenic differences in the MLC; this was apparent when the syngeneic cultures were compared to the allogeneic response in the presence of the lowest concentration of drug. Second, there was a dose-response-related enhancement of alloresponse by acemannan such that the culture treated with the highest dose, $2.6\times10^{-7}M$, reflects a nearly 60% increase over the non-acemannan culture. The dose response relationship is most convincingly; demonstrated as the enhanced allogeneic response is shown to be significant for each dose of acemannan tested with respect to the no acemannan condition.

To ascertain whether acemannan exerts a specific effect on lymphocyte alloresponse or a nonspecific effect on tritiated thymidine incorporation, the reagent was added at the conclusion of a 7 day mixed lymphocyte culture MLC, 20 minutes before addition of the tracer to the culture. There was no effect of acemannan when added in this manner as a pulse at the conclusion of the MLC. These data support the specificity of the acemannan effect on enhancement of lymphoid response in the MLC.

2. Acemannan and Monocyte-T Cell Cooperation. To test the hypothesis that acemannan directly stimulates the monocyte responding to alloantigen to provide signal(s) to enhance lymphoid response to antigen and/or mitogen, purified populations of monocytes were incubated for 24 hours with various doses of acemannan. At the conclusion of the incubation the cells were washed extensively and then co-cultured with T lymphocytes at a ratio of 10:1, to simulate the natural ratio found in peripheral blood. Co-cultured cells were stimulated with phytohemagglutinin. The co-cultures with monocytes that were previously incubated with acemannan had a significantly increased mitogenic response in a dose-related fashion.

C. Discussion

This example has explored the capacity of acemannan to function as an immunostimulating drug with important clinical consequence.

Acemannan is believed to be capable of limiting DNA and retrovirus infections that cause significant diseases in animals and in man. For example, in an animal model, acemannan ameliorated feline viral rhinotracheitis. Additional evidence shows that acemannan in vitro and in vivo may be effective against Herpes simplex II virus, the measles virus, and perhaps HIV. Evidence indicates that the immunological mechanism may involve enhancement of the monocyte, both as a phagocytic cell and as a cell that contributes to afferent recognition of antigen. Studies have shown direct enhancement of phagocytic properties of the monocyte, on the one hand, and an increase in the absolute numbers of that important cell, on the other. Mounting evidence supports the concept that acemannan enhances the elaboration by the activated monocyte of the signal substance IL-1.

The studies described in this example were directed specifically at exploring the mechanism by which acemannan may be an immuno-enhancing reagent. Mixed lymphocyte cultures are in vitro models of the manner in which immunocompetent cells participate in response to antigen of the variety that is necessary for recognition and response to virus. In this reaction, there are important monocyte-T-lymphocyte interactions that generate a response to alloantigen. It was this model that was chosen for testing the capacity of the acemannan to function as an immunoactivator.

Acemannan is therefore an important enhancer of the alloantigenic response in MLC. There is a dose-response relationship with enhancement at the highest dose tested of about 60% above basal. This represents not only a statistically significant but also a biologically relevant increase in response to alloantigen and may serve as one means by which the drug can aid the response of the organism to viral assault. This effect of acemannan was shown to be specific for the allogeneic stimulus, provided the drug did not enhance either basal response to self (syngeneic MLC) or non-specific incorporation of a tracer DNA precursor, tritiated thymidine, when drug was added at the conclusion of the MLC.

A second series of experiments tested the hypothesis that monocyte-T-lymphocyte interactions may be, at least in part, responsible for the heightened alloresponse in the MLC. In this series of experiments acemannan was incubated along with monocytes, after which the treated, extensively washed monocytes were mixed with freshly prepared, syngeneic T-lymphocytes that had not been exposed to and would not be exposed to acemannan. These experiments demonstrate the enhancement of T-lymphocyte response to the polyclonal mitogen phytohemagglutinin at a magnitude equal to the response that had been seen previously in the MLC—approximately 55% above baseline and dose-response relationship.

The lowest dose that was tested in the study that was effective in the MLC had no effect in the monocyte experiment. It is not surprising that the threshold dose may be different for the two models tested, polyclonal response to mitogen and alloantigenic response in the MLC. It can also be observed that the monocyte experiment is a more stringent test of the effect of acemannan because it presents a treated cell type, the monocyte, to T cells that then see an immune stimulus in the absence of the drug. While the alloantigenic response may be due solely or in great measure to acemannan-enhanced monocyte production of IL-1, the lesser polyclonal mitogen-enhanced response may be a consequence of an assay of immune stimulations, each with a different threshold response to acemannan.

The dose of acemannan used in these experiments is clinically relevant. The dose range selected was chosen precisely to bracket that concentration of acemannan that could be expected to be achieved in plasma if the drug distributes in extracellular water and is absorbed at the rate of a third of the orally-administered dose, figures that were based on previous pharmacologic studies in dogs. The actual concentrations achievable in man have also been shown to be in this range, further supporting the potential relevance of these studies for clinical practice.

Acemannan was shown by these experiments to cause monocytes to release monocyte-driven signals to enhance T4 cell response to lectin. While acemannan did not enhance lymphocyte response to syngeneic antigens in MLC, it did increase MLC alloantigenic response in a dose-related manner. This response was shown to be an acemannan-specific response at acemannan concentrations achievable in vivo.

This experimental documentation demonstrates that acemannan is an immunoenhancer and biological response modifier in that it increases lymphocyte response to alloantigen. A proposed mechanism of action involves stimulation of monocytes to release IL-1; in the presence of, acemannan, IL-1 has been shown to be released from monocyte cultures. The pharmacologic action of acemannan stimulation of monocytes may explain acemannan activity against viral infection in animals and man.

EXAMPLE 5

Pharmacokinetic Basis for Correlation of Vitro and in Vivo Effectiveness of Acemannan To evaluate the pharmacokinetic behavior of acemannan, $^{14}$C-labelled material was given by IP and IV injection and PO administration. Based on the results of previous pilot work, an aqueous dose of 200 mg $^{14}$C-labelled acemannan/ 200 ml with specific activity of 17.4 cpm/$\mu$g was administered to female dogs (approximately 20 mg/kg). Blood, urine and feces samples were taken at appropriate intervals for 48 hours or longer. Organ and tissue samples were taken after sacrifice, and all samples were analyzed for radioactivity using scintillation spectrometry.

Acemannan's kinetic behavior was typical of that seen with most pharmacologic agents; however, its biologic half-life ($t_{1/2}$) was extraordinarily long. Significant absorption occurred by all three routes of administration. Maximum blood levels were achieved after IV injection followed by IP and then PO. Blood levels, which were immediately maximal at 200 $\mu$g/ml after IV injection, declined with a $t_{1/2}$ of 50–60 hours; plasma levels were approximately twice those of blood. By comparison, after IP injection blood levels peaked at 45 $\mu$g/ml at 24 hours and then declined at a rate similar to that seen with IV; in fact, blood levels were nearly 90% maximal after only 8 hours. With oral administration, blood levels were measurable after 3 hours and peaked at 4–5 $\mu$g/ml. Based on the relatively long half-life in blood, a therapeutic dosing interval of approximately 7 days would be justified, considering the time required for three half-lives.

Radiolabeled acemannan distributed mainly in liver and spleen following IP or IV injection. Liver, marrow, thymus, and lymph nodes were primary sites of distribution after oral dosing, a finding consistent with the immunologic sites of action for acemannan. Levels of radiolabeled compound in tissues sampled after 48–52 hours ranged from a low of approximately 1 $\mu$g/g brain to a high of 85 $\mu$g/g spleen after IV injection. Interestingly, levels in brain and spihal cord were higher (approximately 3 $\mu$g/g tissue) after oral, compared to parenteral, administration. This could be the result of the liver's partial breakdown of the polymer into smaller molecular weight fractions during the first pass, thus rendering it capable of penetrating the blood-brain barrier.

In summary, with respect to clinical pharmacokinetic considerations, the data indicate that $^{14}$C-labelled acemannan (1) reaches peak blood levels within 8 hours or less by all routes studied, (2) has a relatively long biologic half-life, which would allow therapeutic dosing intervals of several days, and (3) achieves measurable levels in all tissue systems evaluated, including the central nervous system.

These pharmacokinetic data indicate that acemannan levels in blood and/or tissue can duplicate those levels known after injection or oral administration to produce therapeutic antitumor or antiviral effects in vitro. For example mice implanted with virally-infected Norman Murine Myxosarcoma (NMM) cells and injected IP within 24 hours with 1 mg/kg of acemannan showed 35% survival after 60 days compared to 0% survival in NMM-treated control mice (Peng et al., submitted for publication, 1990). Expected peak blood levels at an IP dose of 1 mg/kg would be on the order of 2 $\mu$g/ml (45 $\mu$g/ml$\times$½₀ mg/kg). Acemannan added to cultures of T-lymphocytes at a concentration of only 0.15 $\mu$g/ml ($2.6^{10-9}$ M; 60,000 MW) increased the generation of cytotoxic T-cells 230% and increased the functional capacity of generated cytotoxic T-cells by 138% to destroy target cells against which they had been sensitized [Womble et al., Int, J. Immunopharmac, 10(8):967–974 (1988)]. Cytotoxic T-cells are thought to be generated against tumor cells like NMM cells.

Blood levels of 4–5 $\mu$g/ml obtained after oral administration of acemannan are also significant, since they correspond to the concentration of acemannan that gives optimal synergism with Zidovudine® (AZT) in vitro. For example, alone 0.001 $\mu$g/ml AZT or 3.2 $\mu$g/ml acemannan increased the viability of CEM cells infected with HTLV-II$_{RFII}$ virus by no more than 10%. Together the protective effect of the antiviral combination exceeded 70%. Similarly, a combination of 0.1 $\mu$g/ml of AZT and 1 mg/ml acemannan resulted in a protective effect exceeding 80% (Kemp et al. submitted for publication1990).

Thus, in conclusion, this pharmacokinetic study demonstrates that acemannan concentrations at least as great as those known to work in vitro are attainable in vivo.

EXAMPLE 6

Report of Two Initial Clinical Pilot Studies of Acemannan in HIV-1-Infected Patients Before the discovery that infection with human immunodeficiency virus type 1 (HIV-1) posed a worldwide health threat, there had been only limited development of antiviral drugs. Despite the recognition that more than 60% of all illnesses in developing countries are caused by defined viral diseases, very little progress had been achieved in this area. Treatment for the most part consisted of the application of palliative measures designed to provide comfort and relief of symptoms rather than to interfere with the replication of viruses. The pandemic of AIDS, because of the total ineffectiveness of palliative or symptomatic treatment, has resulted in the initiation of unprecedented research into new antiviral compounds targeted to interfere with the replication cycle of HIV.

In the case of the human immunodeficiency viruses, most attention has been directed towards synthesis and development of 2',3'-dideoxynucleoside analogs, a class of antivirals that inhibit the virus-encoded reverse transcriptase. One of these compounds, AZT, remains the only drug approved for the treatment of AIDS. Unfortunately, numerous studies have demonstrated that the compound is extremely toxic in vivo, and its efficacy, although high in vitro, may be considerably less so in vivo [Richman et al., N. Engl. J. Med., 317:192–197 (1987)].

Two studies assessed the response of human immunodeficiency virus type 1 (HIV-1) infection to acemannan and determined whether laboratory values could be used to predict response to treatment. The protocol was submitted to the FDA, as an individual physician investigational new drug exemption and approved by the Institutional Review Board of the Dallas-Ft. Worth Medical Center. Subjects who were HIV-1 antibody positive and symptomatic were treated with approximately 400–800 mg oral acemannan daily and evaluated clinically using modified Walter Reed (MWR) clinical scoring. CD4/CD8 lymphocyte counts and HIV-1 (p24) core antigen levels indicated immune competence and active virus load. In the first study, the 15 original subjects had an average MWR of 5.6, but after 350 days of therapy the surviving 13 had an average of 1.8. CD4 levels in ten subjects increased from 346/mm$^3$ to 471/mm$^3$ within 90 days and to 610/mm$^3$ at 180 days. Five of the 15 patients had detectable serum core antigen; by 350 days only 3 of 13 had detectable, but reduced, serum antigen. Data from this first study suggested that values for CD4 and serum antigen levels could predict the response to acemannan. A second study with 26 subjects confirmed this. The aggregate group had an average MWR of 3.0 at the start, and 90 days later their average was 1.8. The CD4 levels of 16 "responders" rose from 313/mm$^3$ to 372/mm$^3$ during this period, but in 10 others went from 63/mm$^3$ to only 77/mm$^3$. Fifteen of 16 individuals predicted to respond favorably had improved MWR, increased CD4 counts and reduced antigen, indicating that the extent of immunosuppression and viral load influences response to therapy.

EXAMPLE 7

A Phase II Study of Acemannan Alone and with AZT Among Symptomatic and Asymptomatic HIV patients Forty-seven HIV+ patients (23 asymptomatic patients, 24 ARC patients) participated in a double-blind randomized phase II study of acemannan. The protocol was approved by the relevant ethical committees of the Hospital St. Pierre in Brussels, Belgium. In order to evaluate safety and tolerance, with or without concomitant AZT therapy, acemannan was administered during 24 weeks at a daily dose of 1000 mg (2 capsules of 125 mg, 4 times daily). The 23 asymptomatic patients were blindly allocated to receive either acemannan (11 patients, group 1) or placebo (12 patients, group 2). Of the 24 ARC patients who received 1000 mg AZT daily during the study, 12 patients (group 3) also received acemannan 1000 mg (2 capsules of 125 mg, 4 times daily) and 12 patients (group 4) also received placebo. Thirty-three out of 47 patients (70%) completed the 24-week study period (respectively 6, 9, 9 and 9 in the 4 groups). Reasons for withdrawals were: clinical evolution (8 patients: 3, 3, 0, 2), patients' own will (5 patients: 2, 0, 2, 1), or death (1 patient committed suicide in group 3). None of the patients dropped from the protocol because of side effects or poor tolerance. There was a statistically significant difference in the incidence of adverse drug reactions, mainly nausea, between groups 1&2 and 3&4, due to AZT therapy. No difference occurred between acemannan groups (1&3) and placebo groups (2&4). Hematological data were statistically comparable among 4 groups at study entry. At week 24 there were statistically significant differences for red blood cell count and mean corpuscular volume between patients with or without AZT but no difference between placebo and acemannan patients. There was no liver or renal toxicity among the 4 groups.

The 12 patients treated with AZT and acemannan (group 3) showed a statistically significant improvement of Karnofsky score (K) after therapy (p<0.008) (mean K=84 at entry, 90 at exit) when compared to patients treated with AZT alone (group 4) (mean K=81 at entry, 83 at exit). There was no statistically significant difference between group 3 and 4 regarding occurrence of adverse events although 2 patients treated with AZT alone developed AIDS (1 Kaposi, 1 esophageal candidiasis) compared to none under combination therapy. Comparison of CD4 cell count of AZT-treated patients showed a significantly greater improvement (p=0.01) at the end of the study among those treated with combination therapy (mean CD4 263/mm3 at entry, 369/mm3 at exit in group 3 compared to 145/mm3 at entry and 252/mm3 at exit in group 4). We conclude that acemannan is a very well-tolerated compound with no biological toxicity and that among ARC patients acemannan would have a role as adjunctive therapy to AZT in the management of HIV infection.

EXAMPLE 8

Concentration-dependent Inhibition of HIV-1 Replication and Pathogenesis by Acemannan In Vitro Peripheral blood mononuclear (PBM) cells and two defined CD4+ cell lines, MT-2 and CEM-SS, were used as target cells for HIV-1 infections and treated with various concentrations of acemannan. Viabilities were determined either by the trypan blue dye-exclusion test or by metabolic conversion of MTT [3-(4,5-dimethylthiazol-2-yl)-2,5 diphenyl tetrazolium bromide] to formazan by viable cells. Virus replication and load were measured by hybridization of cell-associated viral RNA and cell-free RNA with an HIV-1 probe prepared from the POL gene. Protection of PBM cells by acemannan treatment was shown to be concentration-dependent. Percent protection ranged from 14–100% for cells treated with 3.2–100 µg/ml of acemannan. Protection by acemannan treatment of HIV-1-infected MT-2 cells was not only concentration-dependent but also multiplicity of infection-(MOI) dependent. Protection of CEM-SS cells infected at an MOI=0.01 and treated with 62.5 µg/ml of acemannan exceeded 85%. In addition to an increase in cell viability, a concentration-dependent reduction in syncytium formation was observed. Syncytia could not be detected in cultures treated with ≧62.5 µ/ml of acemannan. A concentration-dependent reduction in virus replication was also observed for treated PBM cells. Treatment of PBM cells with concentrations of acemannan ≧62.5 µg/ml resulted in a 95–100% reduction in detectable cell-associated viral RNA. Treatment of virus-infected CEM-SS cells with acemannan concentrations ≧62.5 µg/ml caused >60% reduction in cell-free virus. Acemannan treatment inhibits virus-induced cell fusion, increases infected cell viability, reduces virus load and suppresses production and/or release of free virus. Cytotoxicity due to acemannan was not observed at any test concentration.

EXAMPLE 9

Synergistic Antiviral Effects of Acemannan In Combination with AZT (Zidovudine)

The protective effects of combinations of AZT and acemannan were measured in vitro using HIV-1-infected MT-2 cells at a MOI of 0.03. Checkerboard titration of the two drugs indicated that a synergistic protective effect occurred. Concentrations of acemannan of less than 125 µg/ml were most effective in this respect.

It is now clearly recognized that some form of combination chemotherapy will be required in order to increase the efficacy of AZT while limiting its long term toxic effects and circumventing the further development of resistant HIV strains. For this reason, as well as the obvious beneficial effects of acemannan on clinical HIV infection when administered with AZT, it was decided to determine whether these two compounds had a synergistic inhibitory effect on HIV replication in vitro.

Virus Strains - The HTLV-IIIB strain of HIV-1 was obtained from Dr. R. Gallo, NIH, Bethesda, Md. Viral stocks were prepared by propagating the virus in H9 lymphoid cells. A stock preparation of the virus was stored at −80° C. The 50% tissue culture infective dose (TCID50)/ml of cell-free virus pool stock was determined by end-point titration using MT-2 cells. Multiplicity of infection (MOI) was determined by the method of Reed and Muench.

Cell Lines - MT-2 cells were propagated in RPMI-1640 supplemented with 2 mM L-glutamine and 15% (v/v) fetal bovine serum. MT-2 cells naturally express CD4 on their surface and are thus good target cells for HIV-1 infection. In addition, they rapidly undergo cytolysis at low levels of virus replication.

Primary testing of antiviral activity - MT-2 cells were first treated with polybrene (2 mg/ml) for 30 min and then infected with HIV at a MOI of 0.03. After virus absorption, the cells were pelleted and resuspended in complete medium. The infected cells were then dispensed ($2 \times 10^4$ cells/100 µl/well) into 96-well microtiter plates. Each drug was diluted in medium from a stock solution of 2 mg/ml in six serial half $\log_{10}$ dilutions. AZT was tested from the highest concentration of 10 µg/ml to a low concentration of 0.032 µg/ml. Acemannan was tested at 500 µg/ml and diluted down to a low concentration of 15.62 µg/ml. Parallel assays were performed in triplicate, and drug cytotoxicity was measured at parallel concentrations in duplicate. Controls included uninfected, untreated cell cultures and virus-infected, untreated cultures. Plates were incubated for 7 days in a humidified atmosphere of 5% CO2 in air. On day 7 post-infection, cell viability was measured by the addition of MET (450 µg/ml) to the test plates. A solution of 10% sodium dodecyl sulfate in 0.01N HCl was then added to dissolve the MTT formazan that was produced. The color intensity is a function of the amount of formazan produced which, in turn, is proportional to the number of viable cells in each well. Plates were read at a wavelength of 570 nm on a Vmax plate reader (Molecular Devices, Inc.). The percent change in cell viability was calculated using the following formula:

$$\% \text{ change in cell viability} = \frac{(TI - TO) - (OI - TO)}{(OO - TO) - (OI - TO)} \times 100$$

where:
TI is the optical density (OD) in treated, infected cells,
TO is the OD in treated, uninfected cells,
OI is the OD in untreated, infected cells, and
OO is the OD in untreated, uninfected cells.

An antiviral activity of acemannan-AZT combinations-Antiviral activity of acemannan in combination with AZT at various concentrations was evaluated using the microtiter infection assay described above. For each mixture, defined amounts of the test compounds were dissolved in RPMI-1640, and 0.1 ml of each dilution was added to test wells. Combinations were evaluated in duplicate, and treated uninfected controls were used to determine drug cytotoxicity. Each compound was also evaluated alone at non-cytotoxic concentrations. Thus AZT was tested at concentrations ranging from 0.32 to 10 µg/ml and acemannan was evaluated at concentrations ranging from 15.62 to 500 µg/ml. The percent change in cell viability was determined as described above.

Figure 2:
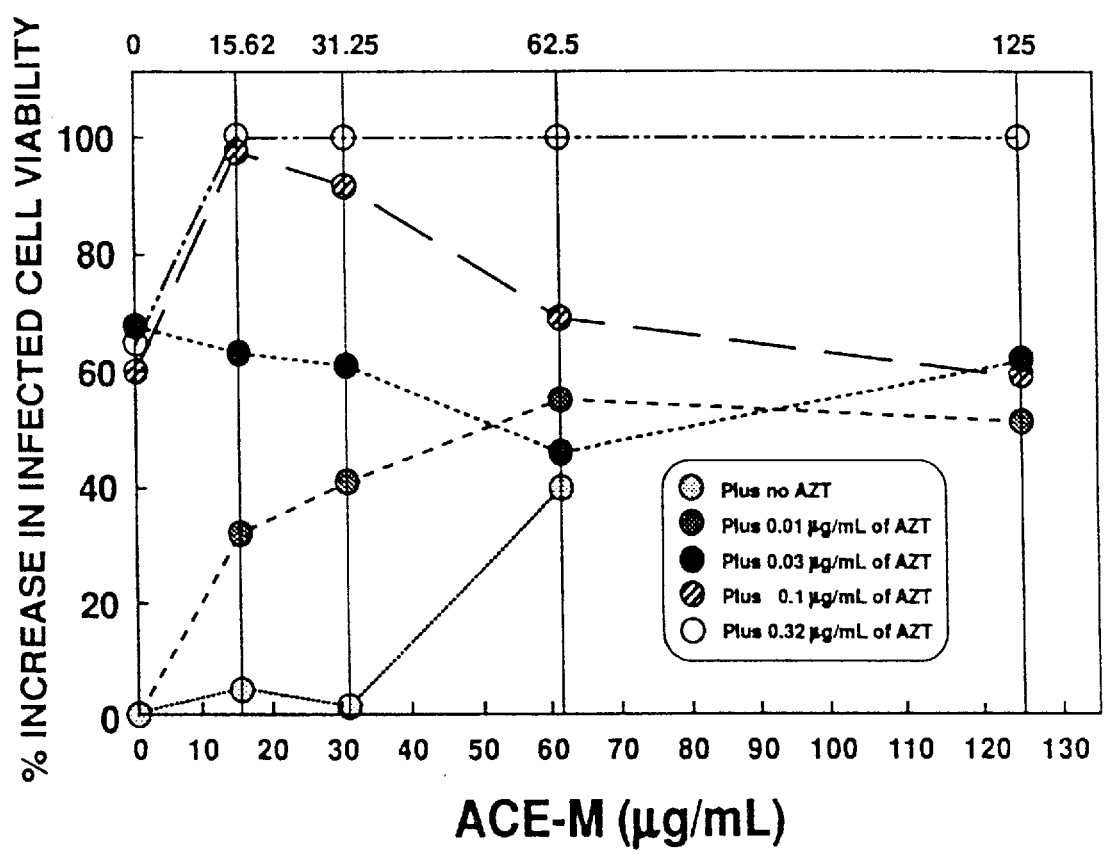
FIG. 2 shows synergistic antiviral effects of acemannan and AZT as quantified by the percent increase in viability of HIV-infected MT-2 cells.

The effect of AZT-acemannan combinations on HIV-infected MT-2 cell viability is shown in FIGS. 1 and 2.

Acemannan alone conferred a maximum of 40% protection at a dose of 60 µg/ml. At higher doses the protective effect was erratic. AZT alone conferred a maximum of 60–67% protection at doses ranging from 0.03 to 0.32 µg/ml. Cytopathic effects could, however, be completely abolished by 0.32 µg/ml AZT in the presence of 15.62 to 250 µg/ml acemannan.

The data presented here clearly show that AZT and acemannan exercise a synergistic protective effect on MT-2 cells infected in vitro with HIV-1. These results support the clinical evidence for the same effect. Synergism, by definition, implies that the effect of the mixture of compounds is greater than the sum of their effects when acting alone. Thus when 0.01 µg/ml of AZT was mixed with 15.62 µg/ml acemannan (neither of which was protective on its own), 32% cell viability was achieved. Indeed, at unprotective acemannan concentrations of 31.25 and 15.62 µg/ml, significant enhancement in the protective effect of 0.1 µg/ml AZT was seen.

When 0.32 µg/ml AZT (65% protection) was mixed with 62.5 µg/ml acemannan (40% protection), the mixture gave 100% protection. Obviously, in this case any synergistic effect would be hidden because it is not possible to detect a viability over 100% and the effect gives a spurious appearance of additivity.

The appearance of this synergistic effect implies that AZT and acemannan interfere with viral replication at different stages of its cycle. As a result, a sublethal hit at one stage in the HIV replication cycle may complement a hit at another stage. The combination of two hits collectively exerts a lethal effect on the virus. AZT, of course, is well recognized as an inhibitor of the reverse transcriptase of the virus. Acemannan, on the other hand, possibly interferes with glycosylation and HIV envelope processing.

EXAMPLE 10

Acemannan used in Treating Cutaneous Ulcers

An 83-year-old female patient, TB, developed an ulcer, 25 mm in diameter, on the lateral margin of her left foot. The ulcer had been present for several months and had failed to respond to several treatment regimens.

The wound was treated with the product of Example 3 of U.S. Pat. No. 4,735,935 and the product of Example 7 of U.S. Pat. No. 4,735,935 using a three-times-daily treatment schedule. The clean wound was soaked for 15 minutes with the product of Example 2 of U.S. Pat. No. 4,735,935. Excessive product was absorbed from the wound with a dry, sterile 4×4 gauze. The product of Example 7 of U.S. Pat. No. 4,735,935 was then applied in a quantity sufficient to cover the wound and to prevent wound dehydration between dressing changes.

The progression of wound healing was measured by interval photographs and planimetry of the wound defect. The progression of wound closure is shown in Table 11.

TABLE 11

PROGRESSION OF WOUND HEALING

| Day | Wound Area (Sq. In.) | Percentage of Healing |
| --- | --- | --- |
| 1 | 1.24 | 0.00 |
| 28 | 0.51 | 58.87 |
| 77 | 0.29 | 76.61 |
| 83 | 0.12 | 90.32 |
| 97 | 0.00 | 100.00 |

The epidermal defect was substantially closed in 12 weeks; complete closure occurred in 14 weeks.

EXAMPLE 11

Acemannan Used as a Treatment for TIC Douloureux

Tic douloureux, or neuralgia of the fifth cranial nerve, is characterized by attacks of severe, unbearable pain over one or more branches of the trigeminal nerve. The pain usually is transient, and attacks may be precipitated by touching some area of the face—the so-called trigger zone.

The cause and cure of this painful disease are unknown. Several attempts to treat the disorder have met with little or no success. Various treatments have included analgesics, phenytoin, peripheral avulsion of the involved nerve branch as it leaves the skull, and injection of 98% alcohol into the gasserian ganglion.

A more drastic treatment—sectioning the sensory root of the nerve proximal to the ganglion—leaves the patient permanently without sensation in the area supplied by the sectioned nerve. Another recent treatment attempt uses carbamazepine and phenoliophendylate injections. However, these injections can be complicated by unpleasant numbness and serious side effects.

None of the previously cited treatments is desirable.

A 43-year-old woman was diagnosed as having tic douloureux. The affected area included the first and third divisions of the trigeminal nerve on the right side.

The patient could trigger the pain by brushing or combing her hair on the right side. She had been treated unsuccessfully with diazepam (Valium), antihistamines, analgesics, propranolol hydrochloride (Inderal) and phenobarbital. The patient said she had not had a pain-free day since the onset of the disease.

The proposed therapy involved drinking 1 to 2 oz. of the product of Example 2 U.S. Pat. No. 4,735,935 daily for 3 months. After that period, the therapy was evaluated.

The patient's pain diminished significantly within 2 weeks of initiating therapy. She said she felt well for a few weeks. However, she then went on a 2-week trip during which she did not drink the product, and symptoms and pain returned. After she resumed the medication, however, the pain disappeared within a few days. For the next few weeks, she again felt well.

After drinking the product daily for more than 6 months without interruption, she reports that she can brush and comb her hair without triggering the pain. Her appearance has improved, and she says she feels better than ever before.

EXAMPLE 12

An Exploratory Clinical Pilot Study Utilizing Acemannan in Inflammatory Bowel Disease Inflammatory bowel disease (IBD) is a collective term for Crohn's disease, ulcerative colitis and other conditions of the gastrointestinal tract. Crohn's occurs mainly in the ileum and colon, whereas ulcerative colitis is limited to the colon. At least three credible hypotheses have been set forth to explain the etiology of IBD. One holds that an unknown infectious agent, such as a slowly growing bacterium or virus, triggers the immune system and sets up a chronic inflammatory response. The second holds that this same sequence of events is caused by a toxic substance, such as food-borne or environmental contaminants. The third hypothesis suggests that the inflammatory response is an autoimmune condition. However, the precise cause(s) of the disease remains unknown.

A. Patient Selection.

This study protocol was submitted to the FDA as an individual physician investigational new drug exemption and approved by the Institutional Review Board of the Dallas-Ft. Worth Medical Center. Patients were selected without regard to age, sex, racial or ethnic background, and all patients were volunteers. Each received an informed consent briefing by the physician, and each was required to sign an informed consent form.

Only patients with a combination of the following symptoms and signs of IBD were admitted:
1. Diarrhea (number of bowel movements)
2. Blood in stool (occult blood)
3. Excess mucus production
4. Spontaneous abdominal pain
5. Abdominal pain on palpation
6. Constant cramping
7. Other (weight loss, etc.)

The above symptoms were used to arrive at a clinical evaluation score of 0 to 7 with 1 indicating a single symptom and 7 indicating all symptoms were present. A score of 0 indicated the patient was asymptomatic.

B. Endoscopic Evaluation.

Endoscopy was utilized to score patients pre- and post-therapy according to the following criteria:
1. Ulcerations
    -Confluent
    -Spotty
    -Linear
    -Segmental
2. Hyperemia
3. Exudate
4. Other The same experienced endoscopist scored listed mucosal appearances according to distribution and severity. A score of 0 indicated the patient had normal appearing mucosa, 5 denoted most severe.

C. Histological Evaluations.

Scoring of histological findings were recorded as follows:
  Exudate, Ulcerated mucosa, Edema, Plasma cells, Lymphocytes,
  Polymorphonuclear cells, Eosinophils, Granulomas, Crypt abscess,
  Fibrosis, Other The above clinical, endoscopic and histopathological criteria were used to grade manifestations of IBD and to quantify response to acemannan treatment. Physical examinations with endoscopy and histological sampling were limited to regularly scheduled visits. Patients were permitted to withdraw at any time without cause and without impact upon their usual therapy. Acemannan was furnished by Carrington Laboratories, Inc.

D. Clinical Results.

Nine IBD patients were admitted and were treated daily with 200 mg acemannan in capsules. Patients ranged in age from 14 to 46 years and included four females and five males. Typically, the patients had abdominal pain, diarrhea or multiple bowel movements; the stools were usually bloody and watery with an increase in mucus production or a combination of these elements. Initial endoscopic examination revealed a spectrum of mucosal alterations ranging from vascular congestion with mucosal friability to focal, extensive and confluent ulcerations, termed "pancolitis." Histological examination of bowel biopsies revealed damage ranging from a non-specific increase in chronic inflammatory cells to frank ulceration with numerous polymorphonuclear cells and eosinophils. Two patients had microgranulomata and crypt abscesses. All patients were presented as nonresponsive to conventional agents, including one or more of the following: Azulfidine, prednisone, 6-mercaptopurine and Flagyl. Imodium and tranquilizers were often added to the above agents.

The response to acemannan medication was uniformly favorable, with all scores improving in all patients. The average pre-and post-medication scores were as follows:

| | |
|---|---|
| Average pre-treatment clinical score | 4.56 (average of nine patients) |
| Average post-treatment clinical score | 0.44 (average of nine patients) |
| Average pre-treatment endoscopic score | 3.88 (average of eight patients) |
| Average post-treatment endoscopic score | 0.00 (average of two patients) |
| Average pre-treatment histological score | 6.25 (average of eight patients) |
| Average post-treatment histological score | N/A (Patients all refused biopsy) |

No adverse effects attributable to acemannan were observed at any time during the study. Some patients who were quite experienced with their own disease expression reported they were virtually free of pain and symptoms within 2–5 days. In others, particularly those with focal segmental disease (Crohn's and ileitis), the effects of acemannan were slower and less dramatic. All patients refused the post-treatment biopsy, and only two patients accepted post-treatment endoscopy. The following reasons were given by the patients: (1) these procedures are uncomfortable, and (2) the cost was not justified because of their improved condition.

Two patients were episodic in their intake of acemannan, taking it only when symptomatic. Both reported relief of symptoms in 24 to 48 hours after consuming the medication; however, mild symptoms returned in 4–6 weeks after discontinuance of acemannan treatment. Subsequently, 2–3 days of acemannan treatment again relieved symptoms. Acemannan provided dramatic clinical improvement in the acute inflammatory phase of the disease.

EXAMPLE 13

The In Vitro Effects of Acemannan on Measles Virus

Measles virus was incubated with various concentrations of acemannan and then added to susceptible cultures of VERO cells. The purpose of this experiment was to determine whether acemannan would inhibit infection or inactivate measles virus treated with acemannan prior to introduction into a susceptible cell culture. Acemannan-treated virus did not infect the VERO monolayer as evidenced by the absence of cytopathic effects (CPE) of the virus at a threshold concentration of 2.5 mg/ml. Complete absence of CPE was achieved at 5 mg/ml of acemannan in the virus inoculum.

African Green Monkey kidney cells (VERO cells) were used as the target cells. Measles virus was titrated to obtain a plaque count of 30–50 plaques/ml (20 TCID units/0.05 ml) on the virus/cell monolayer. Acemannan at different concentrations was then introduced into media containing this fixed amount of virus.

The concentrations of acemannan were made in complete tissue culture medium. An aliquot of rubella attenuated virus vaccine was used for each titration. The mixtures were pre-incubated at 30° C. for one-half hour and added to previously prepared VERO monolayer in tissue culture chambers.

The results of combining measles virus with various concentrations of acemannan incubated five full days on confluent VERO cell monolayers are provided in Table 12.

Repetitious challenges with various concentrations of acemannan showed that a protective concentration was achieved between 2 mg/ml and 4 mg/ml, this being a transition zone for inhibiting measles virus infectivity. Note Table 12. It is apparent that the 5 mg/ml acemannan level consistently provided protection to the VERO cell monolayer challenged with measles virus pretreated with acemannan.

In this pilot study the effect of acemannan on measles virus was evaluated by comparing 1) VERO cells only (negative controls, 2) VERO cells inoculated with measles virus (positive controls), and 3) VERO cells inoculated with measles virus that had been pre-treated with acemannan. A significant reduction in plaque formation occurred in the acemannan-pretreated virus-infected cultures (#3) as determined by plaque count assay. Complete protection of cultures from virus infection was achieved when virus was pretreated with 5 mg/ml acemannan.

TABLE 12

EFFECT OF ACEMANNAN CONCENTRATION

| DATE | DIL | VIRUS DOSE | # | 1 | 2 | 3 | 4 | AV. | INF. |
|---|---|---|---|---|---|---|---|---|---|
| 09/10/86 | 5 | 25 | 34 | 1(?) | | | | 1 | 0 |
| | 2.5 | | | 12.530 | | | | 0 | 0 | 0 |
| | 1.25 | | | 6.2516 | | | | 1 | 1 | 6.25 |
| | 0.625 | | | 3.12512 | | | | 4 | 4 | 33.3 |
| 09/17/86 | 5 | 20 | 100+ | 0 | 0 | | | 0 | 0 |
| | 2.5 | | | 20 | 30 | | | 25 | 25 |
| | 1.25 | | | 60 | 30 | | | 50 | 50 |
| | 0.625 | | | 100+ | 100− | | | 100+ | 100 |
| | 0.3125 | | | 100+ | 100+ | | | 100+ | 100 |
| | 0.1525 | | | 100+ | 100+ | | | 100+ | 100 |
| | | | | | | | | I | |
| 10/08/86 | 5.0 | 20 | 100+ | 0 | 1 | | | 1 | 1 |
| | 4.5 | | | 1 | 0 | | | 1 | 1 |
| | 4.0 | | | 0 | 2 | | | 2 | |
| | 3.5 | | | 10 | 1 | | | 5.5 | 6 |
| | 3.0 | | | 9 | 0 | | | 4.5 | 5 |
| | 2.5 | | | 5 | 9 | | | 7 | 7 |
| | 2.3 | 10 | | 0 | | | | 0 | 0 |
| | 1.0 | 5 | | 0 | | | | 0 | 0 |
| 10/12/86 | 5.0 | 20 | 5.5 | 0 | 0 | 0 | 0 | 0 | 0 |
| | 4.5 | | | 0 | 0 | 0 | 0 | 0 | 0 |
| | 4.0 | | | 0 | 0 | 0 | 0 | 0 | 0 |
| | 3.5 | | | 1 | 0 | 0 | 0 | 0.25 | 4.5 |
| | 3.0 | | | 1 | 0 | 0 | 0 | 0.25 | 4.5 |
| | 2.5 | | | 0 | 1 | 1 | 1 | 0.75 | 11 |
| | 2.5 | 12.5 | | 0 | 0 | 0 | 0 | 0 | 0 |
| | 1.0 | 6.25 | | 0 | 0 | 0 | 0 | 0 | 0 |
| 10/01/86 | 5.0 | 20 | 6.0 | 0 | 0 | | | 0 | 0 |
| | 4.5 | | | 0 | 0 | | | 0 | 0 |
| | 4.0 | | | 0 | 0 | | | 0 | 0 |
| | 3.5 | | | 0 | 2 | | | 1 | 16.6 |
| | 3.0 | | | 1 | 2 | | | 1.5 | 25 |
| | 2.5 | | | 3 | 3 | | | 3 | 50 |
| | 2.5 | 10 | | 0 | 0 | | | 0 | 0 |
| | 1.0 | 5 | | 0 | 0 | | | 0 | 0 |

EXAMPLE 14

Ability of Acenannan to Reverse Measles Virus Infection in Vero Cell Culture

VERO cells were incubated with medium containing 40 TCID/ml of measles virus for various periods of time (0.5 to 6 hours) prior to the addition of 5 mg/ml of acemannan. Incubation with acemannan after cells were exposed to the measles virus did not protect the VERO cells from infection.

VERO cells were incubated for 0.5 to 6 hours with medium containing 40. TCID/ml of measles virus. The VERO cells were then washed with fresh medium to remove any unbound virus. Medium containing 5 mg/ml acemannan was then added to the cultures, and the cultures were examined for cytopathology after five days.

Results of this experiment are shown in Table 13:

TABLE 13

EFFECT OF BRIEF INCUBATION OF VERO CELLS WITH
MEASLES VIRUS FOLLOWED BY ACEMANNAN
TREATMENT

| DATE | DIL | VIRUS DOSE | # | 1 | 2 | 3 | 4 | AV. | INF. |
|---|---|---|---|---|---|---|---|---|---|
| 09/29/86 | 5.0 | OT 20 | L/0.5mL | 25 | 25 | 25 | 10 | 21.25 | |
| | 5.0 | 0.5 hr | | 1 | 3 | 10 | 2 | 3.5 | 100 |
| | 5.0 | 1.0 hr | | 1 | 10 | 9 | 16 | 9 | 16 |
| | 5.0 | 4.0 hr | | 8 | 21 | 25 | 7 | 15.25 | 42 |
| | 5.0 | 6.0 hr | | x | 18 | 15 | 4 | 12.3 | 71 |
| | | | | | | | | | 58 |
| 11/14/86 | 5.0 | OT 20 | L/0.5mL | 13 | 17 | 17 | 25 | 18 | |
| | | 0.5 hr | | | | | | | 100 |
| | | 1.0 hr | | | | | | | |
| | | 4.0 hr | | | | | | | |
| | | 6.0 hr | | | | | | | |
| 06/10/87 | 5.0 | OT 20 | L/0.5mL | 100 | 100 | | 100 | 100 | |
| | 5.0 | 0.5 hr | | 8 | 8 | 10 | 9 | 8.75 | 14 |
| | 5.0 | 1.0 hr | | 10 | 8 | 9 | 11 | 9.5 | 15.5 |
| | 5.0 | 4.0 hr | | 25 | 15 | 25 | 30 | 23.75 | 38 |
| | 5.0 | 6.0 hr | | 24 | 24 | 25 | 31 | 26 | 42 |

Average of two assays for graph 0t = 100–
0.5 hr = 15–
1.0 hr = 28.8–
4.0 hr = 54.5–
6.0 hr = 50–

A lower infection rate was noted in the half-hour and 1-hour acemannan pre-incubation cultures. No clinically significant protection of VERO cells was noted in cultures pre- incubated for longer periods with acemannan.

VERO cells pre-incubated with measles virus were not significantly protected from infection by addition of 5 mg/ml of acemannan after the infection period had ended.

EXAMPLE 15

Project to Determine the Effectiveness of Acemannan of the Induction of a Protective Immune Response in Commercial Poultry Nationally, losses from disease and management related problems cost the poultry industry in excess of $2 billion annually. Infectious agents such as infectious bursal disease virus (IBDV), a retrovirus that induces mortality and/or morbidity associated with immunosuppression, cause severe economic losses to the poultry industry. IBDV specifically targets precursor B-cells in the bursa of Fabricius leading to selective destruction of the humoral arm of the immune system. This causes an immunosuppressed state akin to Acquired Immune Deficiency Syndrome (AIDS).

The poultry industry routinely vaccinates flocks against IBDV by oral administration of live virus or by subcutaneous injection of inactivated virus. Although both methods of vaccination may effectively elicit an immune response, inherent problems associated with the use of vaccines are introduced. Live virus vaccines are more effective in the elicitation of a protective immune response to a specific strain, but the virus itself may revert to virulence, or replication of the vaccine strain may cause transient immunosuppression leading to increased susceptibility of the flock to secondary pathogens. Killed virus vaccines do not have the same problems as those associated with live virus vaccines, but immune responsiveness is diminished and is dose-dependent. Numerous alternatives to vaccination that involve complicated high-tech solutions are being evaluated, but directed modulation of the immune response by inclusion of an additional component in a killed-virus vaccine represents a potentially simple solution.

Acemannan, on the basis of preliminary observations, acts as an immunomodulator, and this project was designed to determine whether this compound stimulates the immune response to a killed infectious IBDV vaccine.

A. Animals

Chicks hatched from eggs purchased from SPAFAS, Inc. were used for all experiments. Eggs were hatched, and day-old chicks were placed in Horsfall Units.

B. Antigen

BursaVac K (oil emulsion)—acemannan used: Lot #80226–001; resuspended at 1 or 2 mg/ml (see experimental design)

C. Experimental Design:

Study #1 (Group 1). For Study #1, 25 2-week-old chicks were divided into five groups. The chicks in each group were vaccinated as follows:

Group 1 - control, sham inoculated

Group 2- inoculated subcutaneously over the back with 0.5 ml of oil emulsion vaccine Group 3 - inoculated subcutaneously with 0.25 ml of oil emulsion vaccine (Bio-Burs K; Key Vet., Gainesville, Ga.) mixed with the 0.25 ml of acemannan (0.5 mg/ml) suspended in water (1:1 )

Group 4 - inoculated orally with 0.5 ml of microcapsules suspended in acidic water Group 5 - inoculated orally with 0.5 ml of microcapsules suspended in acidic water with 0.5 mg of acemannan Study #2 (Group 2). For Study #2, 117 1-week-old SPF chicks were divided into six groups. The chicks in each group were vaccinated as follows:

Group 1 - control, sham inoculated

Group 2 - inoculated subcutaneously over the back with 0.5 ml of acemannan (2 mg/ml) suspended in water Group 3 - inoculated subcutaneously over the back with 0.5 ml of oil emulsion vaccine (Bio-Burs K; Key VeT, Gainesville, Ga.)

Group 4 - inoculated subcutaneously over the back with 0.25 ml of oil emulsion vaccine mixed with 0.25 ml of acemannan (1 mg/ml) suspended in water (1:1)

Group 5 - inoculated subcutaneously over the back with 0.25 ml of oil emulsion vaccine mixed with 0.25 ml of acemannan (2 mg/ml) suspended in water (1:1)

Group 6 - inoculated subcutaneously over the back with 0.5 ml of oil emulsion vaccine and over the femoral region with 0.5 ml of acemannan (2 mg/ml) suspended in water For both studies serum was collected from each chick at weekly intervals, and serum IBDV ELISA titers were determined using commercially available AgriTech IBDV ELISA kits. FlockChek software, a program marketed by AgriTech Inc., was also used in determining titers.

D. Results

Chicks exhibited no discomfort or side effects as a result of subcutaneous or peroral administration of acemannan suspended in water or oil emulsion.

For Study #1 (Group 1) mean ELISA titers are presented through the sixth week following vaccination in Table 14:

TABLE 14

IMMUNOSTIMULATORY EFFECTS OF ACEMANNAN: STUDY #1

| | Present | IBDV ELISA TITERS DAYS POST-VACCINATION | | | | | | |
|---|---|---|---|---|---|---|---|---|
| Group | Antigen | 0 | 7 | 14 | 21 | 28 | 35 | 42 |
| #1 | Cont | 0 | 0 | 0 | 0 | 7 | 107 | 191 |
| #2 | Em | 0 | 0 | 54 | 372 | 556 | 218 | 4983 |
| #3 | Em & Ca | 0 | 5 | 231 | 1142 | 2276 | 4508 | 3101 |
| #4 | Mic | 0 | 0 | 0 | 2 | 5 | 61 | 127 |
| #5 | Mic & Ca | 0 | 0 | 1 | 0 | 13 | 150 | 0 |

Two weeks after primary vaccinations, titers to IBDV started to rise in chicks treated with oil emulsion or oil emulsion supplemented with acemannan. Chicks treated with the oil emulsion vaccine supplemented with acemannan had an overall mean titer approximately 3.9 times higher than those vaccinated with oil emulsion vaccine. Three weeks after vaccination the chicks were revaccinated, with each chick receiving the same antigen mixture presented in the primary vaccination. One week after secondary vaccination, the difference in mean titer ratio had increased to approximately 4.1. Two weeks after the secondary injection, when mean titers for both groups had reached their peak, the ratio fell to approximately 2.1. By 3 weeks after secondary vaccination, mean titers for both vaccinated groups had begun to decrease, but the decrease in titer for chicks vaccinated with oil emulsion alone was more precipitous, with a drop in titer of 55% as compared to 319% for chicks vaccinated with oil emulsion supplemented with acemannan. Maintenance of the higher titer in birds treated with oil emulsion supplemented with acemannan appears due to prolonged immunostimulatory actions of acemannan.

Three weeks after the secondary vaccination, chicks from the oil emulsion vaccine group (#2) and the oil emulsion vaccine supplemented with acemannan group (#3) were redivided into two groups (A and B). Group A chicks were challenged with the homologous live vaccine strain, and Group B chicks were challenged with a virulent field strain. Three days after challenge, all chicks were necropsied. There was no effect on the immune system in Group A chicks challenged with the vaccine strain. But all Group B chicks had lesions as demonstrated by histopathology. These were the expected results, but if chicks given only a primary vaccination had been challenged, it is likely that a greater preponderance of lesions in chicks given only the oil emulsion vaccine would have been seen. If the chicks had been vaccinated with the live virus vaccine, lesions in the lymphoid organs would have been seen in chicks resistant to homologous virus challenge.

For Study #2, group sizes and the vaccination protocols were changed. As may be seen from Table 15, results were inconsistent:

TABLE 15

IMMUNOSTIMULATORY EFFECTS OF ACEMANNAN: STUDY #2

| | Present | IBDV ELISA TITERS DAYS POST-VACCINATION | | | |
|---|---|---|---|---|---|
| Group | Antigen | 0 | 7 | 14 | Std. Dev. |
| #1 | Cont | 0 | 11 | 1 | S.D. 0 |
| #2 | Ca(0.5 mg) | 11 | 37 | 1 | S.D. 0 |
| #3 | Em | 21 | 11 | 181 | S.D. 571 |
| #4 | Em & 0.25 mg Ca | 46 | 0 | 5 | S.D. 11 |
| #5 | Em & 0.5 mg Ca | 188 | 0 | 279 | S.D. 824 |
| #6 | EmRt & 0.5 mg CaLt | 36 | 79 | 504 | S.D. 842 |

Differences in the birds were initially noticed two weeks after injection. There were more runts than would be expected, and some of the sites where the chicks were banded appeared to be infected; they had pressure necrosis, which would result in toxin release, in addition to secondary bacterial infection. In an effort to circumvent the latter problem the chicks were rebanded and treated with a topical antibiotic. However, the problems described would probably cause overall immunosuppression, thus voiding the results of this study. Therefore, the experiment was terminated.

In spite of the negative factors associated with Study #2, acemannan caused an overall stimulatory effect of the immune system, i.e., as an enhanced immune response to test antigens administered at sites remote from the site of acemannan administration. Although the initial impression was that acemannan had to be mixed with the oil emulsion vaccine, it appears that an enhanced immune response was elicited when the antigen and acemannan were presented separately as well. This result allows for exploration of alternative vaccination methodologies and applications for this compound.

Acemannan has adjuvant properties. It increases the persistence or effective presentation of IBDV antigen within the body, possibly leading to release of lymphokines and an enhanced lymphocyte response.

EXAMPLE 16

Acemannan Used for the Treatnment for Malabsorption Syndrome

Malabsorption syndromes in man cause a wasting condition that can eventually result in death. Specific human syndromes such as sprue and celiac disease can be ameliorated if certain grains containing complex polysaccharides and enzyme-inhibiting peptides are withdrawn from the diet. The result of this diet change is to reduce the symptoms. However, a major physiological problem remains for the patient; maturation of small bowel intestinal mucosa is arrested due to inhibition in synthesis of glycoproteins essential for cell maturation. This failure of small bowel interaction reduces absorption surface and further results in failure to absorb essential amino acids, fatty acids, minerals, vitamins and other critical molecular substances present in the diet.

A 56-year-old male who had lost over 40 pounds from chronic gluten-sensitive sprue had a rapid reduction in chronic diarrhea followed by progressive weight gain after taking oral acemannan estimated at 500 to 800 mg/day.

Mannose is required for glycoprotein synthesis. Providing additional mannose in a diet predictably shifts the velocity of $K_m$, increasing the rate of glycoprotein synthesis. Enzyme synthesis is promoted by the availability of the critical mannose substrate that fosters ribosomal/glycoprotein synthesis by mannose-metabolizing enzymes. This increase in glycoprotein synthesis and availability results in small intestine mucosal cell maturation and reduction in symptoms associated with sprue and celiac disease. In addition, this thermodynamic shift in glycoprotein synthesis has applications to other categories of disease for which no effective existing therapy exists.

EXAMPLE 17

Acemannan as A Treatment for the Symptoms Associated with Multiple Sclerosis

Multiple sclerosis (MS) is a neurological disease of unknown etiology and no effective treatment. Analysis of patient data and demographics indicate the disease is most likely initiated by an infectious agent, probably of viral origin. Analysis of central nervous system lesions, spinal fluid and serum suggests that an autoimmune component is also present. This autoimmune response results in myelin sheath degradation.

A 36-year-old patient who had suffered from multiple sclerosis for more than 6 years and had been bedridden for 4 months was treated with steroids after which walking in the house was possible with the aid of a walker. A wheelchair was needed for travel outside the home. The attending physician advised the patient that without chemotherapy (including treatment with cytoxan), the patient would return to the bedfast state within 6 months.

The patient elected to discontinue all prescribed therapy and began taking approximately 500 mg oral acemannan daily. The patient observed no change in the status of the disease until about 10 weeks had elapsed at which time she reported feeling better than at any time in the previous year. Two weeks later she was able to walk longer distances using the walker and in one more month was able to walk with the use of only a cane. By the time she was to have been bedridden (as predicted by her physician), she was able to shop several hours at a time using a cane or walker.

The patient has maintained this level for more than 10 months while continuing to consume about 500 mg acemannan per day with no other concurrent therapy.

In 1986, patient F. G. a 57-year-old female presented with a history of leg weakness, progressive loss of voice and multiple other neuromuscular symptoms. At Johns Hopkins Medical School, MS was diagnosed with NMR confirmation. The patient was started on 800 mg/day oral acemannan and an extensive exercise program.

Six weeks after therapy initiation, she was able to go on an ocean cruise with limited physical support. The patient's voice progressively strengthened and other symptoms improved. At 6 months she reported that her neurologist indicated that plaques visualized by NMR techniques had regressed. The patient continues to experience remission of the symptoms associated with MS.

EXAMPLE 18

Acemannan Used as an Antiviral Agent in a Plant

Acemannan was evaluated as an antiviral agent against the LaFrance virus, a major problem in the mushroom farming industry. The compost used was prepared by a modification of the method of Flegg et al. LaFrance virus-infected Agaricus bisporus M8 span was added to prepared compost at 3% of dry matter. The spawned trays were covered with plastic and incubated for 14 days at 24° C. Acemannan was added to spawned compost in a range of doses from 0.01% to 2% (calculated on a dry weight basis) and placed into 11"×7" trays at 1.0 lb dry matter/tray. The material was mixed evenly with the compost by adding both components to the sampling bag and mixing thoroughly. Spawned, treated compost was turned and overlaid with sphagnum peat moss and incubated for a further 7 days at 24° C.; the overlay material was then gently mixed, the plastic replaced, and the trays incubated an additional 10 days. The plastic was then removed and the trays incubated for an additional 7 days at 18° C. in an environmental chamber. Mushrooms were harvested at weekly intervals thereafter for three weeks.

Sporophores were analyzed for double stranded (ds) viral RNA by homogenization in 20 ml STE (1.0M NaCl; 0.5M Trizma base, pH 8.0; and 0.01M EDTA), 20 ml LiCl, and 10 ml 10% SDS. The dsRNA was extracted in phenol and the aqueous phase was passed through a Bio-Rad LC column containing Whatman CF-11. The cellulose-bound dsRNA was washed and then eluted with STE. After precipitation with ethanol and resuspension in citrate solution, an aliquot was characterized by agarose gel electrophoresis. The dsRNA patterns were visualized by ethidium bromide staining. A reduction in dsRNA was shown in the sporophore analyzed from experimental trays containing 0.01% to 1.0% acemannan as compared to untreated controls.

EXAMPLE 19

Acemannan Used as a Treatment for Chronic Fatigue Syndrome

Acemannan has been shown to affect chronic viral syndromes in humans. A 41-year-old female with a 2-year history of markedly debilitating "chronic fatigue syndrome" (CFS) and elevated Epstein-Barr viral titers reported that taking 800 mg/day of acemannan orally for 6 months resulted in complete relief of lethargy. After three excellent months without symptoms, the patient discontinued oral acemannan and there was a slow return of tiredness with fatigue. Resumption of acemannan rapidly alleviated the symptoms of the syndrome.

A physician's sister had a prolonged period of chronic fatigue syndrome with elevated Epstein-Barr antibodies. Multiple clinical evaluation and therapeutic regimens had no effect. The patient started consuming 800 mg acemannan daily and reported a marked improvement followed by elimination of symptoms after 2–3 months of acemannan therapy.

EXAMPLE 20

Combination of Radiation, Chemotherapy and Acemannan for the Treatment of a Tumor of Embryonic Tissue Origin Patient W. H. at the age of 41 presented at a medical center with severe chest pain. Radiographs suggested a mediastinal mass of possible vascular origin and the patient was transferred to a cardiovascular center. There it was determined that a mass extended from the low neck region to the diaphragm, grew between the lungs and involved the base of the heart. Biopsy disclosed a malignant embryonic sinus tract tumor. Treatment with oral acemannan, (approximately 500 mg/day with radiation and chemotherapy) was instituted. Six years past therapy, the patient has a normal chest x-ray and lives a normal, active life. A review of the literature disclosed 20 such tumors with 100% fatality 9 to 12 months post-diagnosis.

EXAMPLE 21

Multi-Drug Combination Chemotherapy and Acemannan Treatment of a Hepatic Tumor

Patient M. A. presented with the chief complaint of inability to zip up his pants or get his belt around his abdomen. Computer axial tomographic (CAT) scans in April 1988 revealed multiple tumors in the liver which extended to the urinary bladder. The liver was largely replaced by over 20 tumor masses up to 10 cm in diameter. A life expectancy of 4 to 6 weeks was given. The patient had been on 800 mg/day oral acemannan for HIV-1 infection. A multiple chemotherapeutic treatment was initiated and the acemannan was continued. The patient had minimal side-effects and toxicity usually associated with cancer chemotherapy. Evaluation at 3 months included a CAT scan that revealed an estimated 60% reduction in tumor mass. At 6 months, 85% reduction in tumor mass was estimated. Only minimal tumor was noted at 12 months, and at 24 months only small scars with questionable tumor mass remained in the liver. All clinical laboratory work was normal and the patient is currently doing well.

EXAMPLE 22

Acemannan Treatment of Skin Tumors Associated with HIV

Patient S. G. presented with two black lesions, palpable on his arm that had been previously diagnosed by biopsy as Kaposi's sarcoma. Acemannan gel with 5% DSMO was topically applied to the skin masses on the arm while similar masses on other parts of the body were not treated. Reexamination at weekly intervals revealed noticeable flattening and depigmentation of the lesions. Sixty days after therapy was begun, only flat scarred areas remained. Subsequent treatment of other lesions on the same patient showed the same results.

Patient T. P. D. presented with a palpable ankle lesion with pigmentation of classic Kaposi's sarcoma. The lesion was subcutaneously injected with 1 cc recombinant alpha interferon (Roche). The size and pigmentation were improved by 3 days. Topical acemannan gel on a bandage was applied and, by the end of 1 week, no evidence of a lesion remained. There was no scarring or alteration of pigmentation.

EXAMPLE 23

Acemannan Treatment of Premalignant Skin Lesions

Subject W. B., a balding physician, had numerous solar keratoses over sun-exposed skin. Two weeks of nightly applications of acemannan gel to these lesions resulted in removal of the scales, crusts and skin irregularities that were pre-malignant in appearance. This response has been noted in many other mature patients.

EXAMPLE 24

Acemannan Treatment of Edema Associated with Cancer Surgery

In January 1984, patient J. J., a 32-year-old male with unsuccessful surgical resection of a pharyngeal primary tumor, radical neck dissection, radiation and chemotherapy was in unmanageable pain due to total occlusion of the larynx and esophagus. Due to lymphatic blockage, the head was approximately twice normal size and edema had obliterated all facial features. Life was sustained by a feeding gastroscopy and a tracheotomy. Topical acemannan gel (CDWG 0.025%) was applied copiously over the entire head, neck and shoulders every 8 hours (TID). By the third day the edema was noticeably reduced and by the tenth day the excess tissue fluid was gone. Between the 14th and 16th day there developed fluctuant areas in the neck base, angles of the jaw and behind the ears. The skin opened and necrotic tissue began to exude from the areas of former hard, infiltrative, nodular tumor. The patient began to cough up masses of gray-white degenerating tumor. Multiple transfusions were given for the massive hemorrhage which ensued. Slowly, the patient regained the ability to speak, cat soup and breathe through the mouth and nose.

EXAMPLE 25

Combination 5-Fluorouracil and Acemannan Cancer Treatment

Patient C. M. had an abdomino-peritoneal resection of low rectal adenocarcinoma with high mesenteric lymph node metastasis. The patient refused radiation therapy but elected to accept weekly 5-fluorouracil (5-FU) IV infusions and 800 mg oral acemannan/day. The patient did not suffer the oral ulcers, severe fatigue or nausea with vomiting usually associated with 5-FU treatment. After an extensive evaluation by isotopic scans and computerized tomography (CAT), the patient had no detectable adenocarcinoma at 24 months post-surgery and continues to be normal.

EXAMPLE 26

Multi-drug Combination Chemotherapy and Acemannan Cancer Treatment

Patient H. H. had adenocarcinoma of the colon with a resection followed by discovery of rising CEA tumor nodules and CAT scan evidence of a liver nodule. Treatment with oral acemannan (800 mg/day) was begun, along with weekly IV injections of 5-FU (500 mg) dicarbazide (50 mg), and acemannan orally (800 mg). Progressive reduction in tumor size and CEA values occurred with no evidence of side effects or biochemical or hematological toxicity.

In 1990, patient V. G., a 66-year-old male, presented following total pneumonectomy with bone and liver metastasis for squamous carcinoma of bronchiogenic origin. Alkaline and all liver enzymes were elevated more than triple the upper limits of normal. One month's therapy of 500 mg 5-FU and 50 mg dicarbazide IV weekly and 800 mg oral acemannan daily resulted in reduction of the alkaline phosphatase and liver enzymes to half their pre-treatment levels along with improvement of the patient's general condition.

EXAMPLE 27

Multi-drug Combination Chemotherapy and Acemannan Cancer Treatment with Anti-Male Hormone Therapy Patient J. R., a 72-year-old male, presented post-surgery and post-radiation with metastatic adenocarcinoma of the prostate with rising acid phosphatase (PAP) and prostate specific antigen (PSA). The patient was started on oral acemannan (800 mg/day) 5-FU (500 mg) and dicarbazide (50 mg). The rise in tumor markers plateaued, reaching a high of 15 units for PAP and 186 U. for PSA. The anti-hormonal agent Eulexin was added to the regimen. The PAP dropped within 60 days to 3.0 and the PSA to 15. This response was accomplished with no toxicity or side effects at any stage. This patient continues to be monitored while the total regimen is continued.

EXAMPLE 28

Acemannan Treatment of Venomous Animal Bites

Acemannan had been shown to alter the body's response to antigens, toxins, allergens and "self" antigens. Two cases of acemannan gel were sent to Swangi Province in Southern China. The Red Cross received the product to be used for burns, bed sores, stasis ulcers, and diabetic skin ulcerations. Approximately 1 year later the head of the Red Cross wrote to confirm that acemannan gel had been a useful treatment of the above conditions; additionally, he reported that it was the best treatment they had ever used for water snake bite, a common occurrence in the manually-worked rice paddies. Snake bites often become infected and are non-responsive to antibiotics; resulting necrosis from profound ischemia in soft tissue causes considerable loss of skin and muscle tissue. Occlusive dressing of wounds with acemannan gel eliminated the unmanageable infections and apparently helped restore capillary circulation to surrounding tissue. This treatment preserved digits, muscles, nerves and soft tissue.

EXAMPLE 29

Acemannan-Treated Cultures of Fibroblasts Revert to Neonatal Morphology and Function Acemannan-treated cultures of fibroblasts obtained from a 60-year-old man revealed a change in the morphology of these aging cells. This change appeared to evidence a reversal in the aging process in these human cells in vitro.

Longer-term fibroblast cultures treated with acemannan (1 mg/ml) in the culture medium resulted in expression of biochemical and morphological characteristics of neonatal cells.

In 1989, a physician examined biopsies of facial skin from a surgery specimen submitted to the pathology department at Duke University. The biopsy was from Mohl's surgery performed for treatment of skin cancer. Acemannan gel was applied post operatively. The specimen exhibited an unusual pattern of necrobiosis with destruction of damaged collagen fibers and rapid regeneration of young collagen fibers by enlarged fibroblasts. The result was rapid remodelling of the structures in this aged skin specimen.

In 1990, the same physician examined thymuses from dogs given acemannan. These thymuses were 2–6 times larger than the thymuses of the control dogs. Microscopically the thymuses from the treated dogs were hypercellular with evidence of hyperplasia and activation of thymocytes. Increased numbers of T-lymphocytes and "nurse-cell" indicated an apparent expansion in T-lymphocyte clones. The induction of thymus activity and fibroblast activity in tissues of acemannan-treated animals would result in the return to function of age-depleted tissues.

EXAMPLE 30

Acemannan Effect on Cholesterol Levels in Animals and Humans

Male dogs given 855 mg/kg/day of acemannan had a statistically significant reduction in serum cholesterol levels which was observed during a 91-day toxicity study. A similar effect was noted in normal male volunteers given doses of acemannan ranging from 400 mg to 3200 mg per day. An important effect of acemannan therapy which was observed was the statistically significant reduction in serum cholesterol level toward normal values for these subjects. Upon entry into the study, the mean cholesterol concentration of the 24 subjects was 189 mg/dl; it was 174 mg/dl upon exit.

Statistical analysis using the "CRUNCH" Software version of the Wilcoxon Signed-Ranks Tests indicated >98% probability that the drop in cholesterol was not due to chance variation. Cholesterol concentrations in seven of the 24 patients decreased more than 20 mg/dl in 6 days of treatment, and therefore it is difficult to attribute this effect to a simple dietary improvement during the subject's controlled residence during the study.

EXAMPLE 31

Acemannan Treatment of Injury Resulting from Plants

Two competition hunters who had a supply of acemannan for veterinary use took it with them on a trip to Africa. After an episode of diarrhea, the hunters decided to take the acemannan themselves. The acemannan was taken at an 800 mg/day dosage level. The hunters reported that they experienced less diarrhea than other hunters.- Also, because of briars in the bush, the hunters suffered numerous cuts on their arms and legs. The hunters taking acemannan reported that their cuts and scratches seemed to heal virtually overnight. No redness or inflammation developed. All abrasions were totally healed by the time they flew back to the U.S. Other members of the hunting party suffered serious infections of their cuts and abrasions requiring visits to their physicians for systemic and topical antibiotic therapy.

The two hunters taking acemannan had no infections and no scarring.

EXAMPLE 32

Acemannan Treatment of Allergies Resulting From Hypersensitivity to Plants

Acemannan was used to ameliorate the inflammatory effect of plant allergens. Subject H. R. M., with a known family history of seasonal hayfever, experienced annual episodes of itching, burning, congestion and watering of mucosal membranes. Starting in 1988, it was found that 800 mg/day oral acemannan for. 5 days virtually eliminated hayfever symptoms including sinus headaches produced by the swollen nasal mucosa. In 1989, it was found that acemannan gel applied topically to the mucosa of the eyes and nasal passages at bedtime and every 8 hours thereafter resulted in a similar effect and benefit to H. R. M.

Similar results have been seen with topical administration of acemannan to poison ivy lesions in humans and animals. The severity of and the healing time for the lesions were significantly reduced.

EXAMPLE 33

Acemannan Treatment of Allergies Resulting From Hypersensitivity to Chemicals Acemannan was used to ameliorate the inflammatory effect of chemical allergens. Subject T. R., a professional painter, was on the verge of quitting his profession due to wheezing and bronchitis induced by vapors from his paints and solvents. After taking 800 mg/day oral acemannan for 5 days, his symptoms were relieved. The patient continues to consume 800 mg/day of oral acemannan before work each day and is able to continue painting.

EXAMPLE 34

Acemannan Treatment of Symptoms Associated with Asthma

A 76-year-old male, T. T., with a 72-year history of asthma was taking 800 mg acemannan daily for an unrelated condition. After 1 year of therapy, T. T. told the attending physician he had not used his aerosolized bronchodilator for over 1 year and a significant amount was still in the unit. His wife stated that he had averaged 2 units per month for 15 years and had used a hand aerosolizer for 50 years before that for chronic asthma. The patient continues to take 800 mg acemannan daily and no longer has wheezing or chronic bronchitis.

EXAMPLE 35

Acemannan Treatment of Symptoms Associated with Cystic Fibrosis

A college-age female with 6-month history of cystic fibrosis syndrome reported an abrupt return of energy within 2 weeks of instituting oral acemannan therapy at a dose of 800 mg/day.

EXAMPLE 36

Acemannan Treatment of Cytomegalovirus Infection as a Result of HIV Infection

A 27-year-old HIV-1-positive male, M. M., had substernal pain for 2 months unrelieved by medications. An esophagoscopy disclosed an erosion of the distal esophageal mucosa. Histopathological staining of biopsies disclosed cytomegalovirus organisms in the epithelial cells. Three days of 1000 mg oral acemannan administered as a lozenge eliminated all symptoms.

EXAMPLE 37

Acemannan Treatment of Sequela to a Rheumatic Fever Episode

A 25-year-old female, S. M., had the acute onset of arthritis, tendonitis, joint edema, leukocytes, and elevated sedimentation rate following a sore throat caused by an acute episode of post-streptococcal rheumatic fever. The ASO titer was markedly elevated. Her sisters and mother had histories of severe, multiple bouts of acute rheumatic fever with incapacitation lasting for up to a year.

The patient was administered 800 mg/day oral acemannan. Sedimentation rate and white count were normal by week 6 of therapy and all clinical symptoms were gone. The patient returned to a manual labor job requiring high dexterity after 8 weeks of therapy.

EXAMPLE 38

Acemannan Used in the Treatment of Autoimmune Disease

A 21-year-old female (E. M.) with a history of pancytopenia, over 2 years progressive anemia, leukopenia and thrombocytopenia presented for treatment in June 1988. She related a history of failure to respond to therapy offered at eight major medical centers in the U.S. Bone marrow transplant had been offered as the next step in therapy. When first examined, the patient had bruising, petechiae, fatigue, low hemoglobin (6.1 gm %) and low platelets (20,000–25,000/mm$^3$) and total white count of 1,500 cells/mm$^3$. Antibody to her own white cells was reported by a 'specialty clinical pathology laboratory. The patient was placed on 800 mg of oral acemannan for 60 days. Minor improvement in laboratory values was noted and her fatigue was minimally reduced. A hematologist was enlisted to administer low-dose prednisone and horse antithymocyte globulin. The former had previously been ineffective. By October 1988 the patient's hemoglobin was over 10 gm %, white blood count was 3,500 cell/mm$^3$ and platelets were 60,000. By mid-1989, 800 mg/day of oral acemannan was resumed for 6 months. In January 1990 the patient reported hemoglobin 12.7 gm %, platelets 120,000 and white blood count 5,200 cells/mm$^3$. The patient is not on any medication currently and is a professional dancer-choreographer in graduate school.

EXAMPLE 39

Acemannan Treatment of Systemic Lupus Erythematosus

A patient with systemic lupus erythematosus was treated by a New York physician with 800 mg/day of oral acemannan. The physician reported that all symptoms diminished and laboratory values markedly improved after 8 weeks of acemannan therapy. Continued acemannan therapy appeared to control the symptoms associated with this patient's condition.

EXAMPLE 40

Acemannan Treatment of Acute Rheumatoid Arthritis

A physician reported that a series of patients with acute rheumatoid arthritis (RA) had elevated RA latex levels and sedimentation rates. After 6 to 8 weeks of 800 mg/day of oral acemannan, the patients had significantly reduced symptoms and markedly improved clinical laboratory values.

EXAMPLE 41

Acemannan Treatment of Chronic Rheumatoid Arthritis

A 65-year-old female, B. L. H., with a 20-year history of chronic RA, deformed joints, subcutaneous nodules and tendinous nodules suffered with chronic pain. When the patient was seen in the fall of 1988, she had been given numerous treatments including gold shots with little benefit. Oral acemannan (800 mg/day) was recommended. No benefit was reported for 6 months. In mid-1989 the patient reported diarrhea if acemannan was taken more often than twice weekly, but symptoms of arthritis were improving. In time, 800 mg acemannan three times per week was tolerated and symptoms of RA noticeably improved. In January 1990 the patient reported that she had experienced her best 6 months of life in the last 15 years. The effort required and the pain associated with her daily tasks were markedly reduced.

EXAMPLE 42

Acemannan and Antidepressant Therapy of Depression and Anxiety

A psychologist gave 800 mg of oral acemannan per day to patients who had failed to respond to psychotherapy and antidepressant drugs taken for severe depression and anxiety. He reported that by the end of the week he could observe that the patients' emotions had become more stable and that there was a remarkable improvement in attitude for the first time since the patients had been under long-term observation.

EXAMPLE 43

Acemannan Treatment of Feline Leukemia

Feline leukemia (FeLV) is a retrovirus (class oncovirus) infection in which cats present with diverse clinical signs. Infection of the lymphoreticular system is predominant with the majority of animals dying within 3 years. Current treatment for this disease is symptomatic; no cure exists.

Forty-five cats with end-stage FeLV disease were treated by intraperitoneal injection of acemannan weekly for six treatments and observed for 6 more weeks. The cats were monitored by weekly examinations during the treatment period. In addition, laboratory data were obtained at entry, mid-study and at exit from the study.

Sixty-seven percent of the treatment animals improved during the study. The average survival time of animals not responding to acemannan therapy was less than 28 days.

EXAMPLE 44

Acemannan and Antifungal Drug Treatment of Fungal Infections Associated with HIV Three $_{HIV}$-1 patients' records reveal a similar pattern in that these patients developed hairy leukoplakia and/or monilial plaques and/or ulcers of the oral cavity. Their conditions were usually extensive and painful. The use of Ketaconazole had improved the condition of some patients, but others were unresponsive. Within 1 week of adding 800 mg/day oral acemannan to their therapy, the patients reported elimination of these mucocutaneous lesions. Taking acemannan and Ketaconazole for 3 to 5 days cleared the outbreak for weeks to months. Continued acemannan S administration eliminated or reduced outbreaks of the mucocutaneous infections.

EXAMPLE 45

Acemannan and Antiprotozoal Drug Treatment of Pneumocystis Carinii Infection Associated with HIV An HIV-1 study patient receiving 800 mg/day oral acemannan was admitted to an Arkansas veterans hospital for x-ray diagnosis-compatible and sputum-proven Pneumocystis carinii pneumonia (PCP). In the experience of the V.A. Hospital, HIV-1 patients with PCP take 2 or more weeks to respond to therapeutic measures, if they ever respond. The patient responded to 1 week of aerosolized pentamidine and continued acemannan therapy. He was dismissed symptom-free.

EXAMPLE 46

Acemannan and Antibiotic Treatment of Cryptosporidiosis Infection Associated with HIV An HIV-1 patient with chronic diarrhea and weight loss was shown to have the typical acid-fast spores in his stool diagnostic of cryptosporidiosis. The combination of 800 mg/day oral acemannan and 250 mg Q.I.D. ansamycin (rofbutin) daily for 2 weeks rendered the patient free of diarrhea with resulting weight gain.

EXAMPLE 47

Acemannan and Antitubercular Drug Treatment of Resistant Human Tuberculosis Associated with HIV HIV-1 positive patient S. G. suffered progressive weight loss and low-grade fever of unknown etiology. Discovery of retroperitoneal lymphadenopathy and biopsies of the mass eventually revealed a culture of human tuberculosis. The patient had been on 800 mg/day acemannan daily. Institution of antitubercular therapy comprised of 300 mg/day isoniazid, 600 mg/day rifampin, and 1000 mg/day ethambutol resulted in the patient's becoming afebrile within 24 hours and gaining weight within 10 days.

EXAMPLE 48

Acemannan and Antitubercular Drug Treatment of Resistant Avian Tuberculosis Infection in Humans Associated with HIV An HIV-1 patient had continuous diarrhea that eventually was shown by smear and culture to be mycobacterium avian intercellular tuberculosis (MAI). No agent is known to be effective; however, ansamycin was provided by C.D.C. In combination, 250 mg Q.I.D. ansamycin and 800 mg/day oral acemannan resulted in termination of diarrhea in less than 1 week. Within 2 weeks the patient who was losing weight at a rate of 3 to 4 pounds per week began to gain weight. Fatigue and general weakness decreased. In another HIV-1 patient, C. C., who had biopsy and culture-proven MAI, a similar rapid resolution and negative culture tests were obtained after oral acemannan.

EXAMPLE 49

Acemannan and Multidrug Chemotherapy Including Cisplatin Cancer Treatment of Breast Cancer A 38-year-old female, J. F., was five years post-mastectomy for duct cell carcinoma of the breast. The patient appeared pregnant due to ascites of peritoneal metastasis. CAT scan evidence of liver and multiple bone sites of lytic tumor were demonstrable. The patient had delayed chemotherapy and was estimated to be 4 to 6 months from death. The patient was told to start acemannan at an oral dose of 800 mg/day and to start the recommended multiple agent cytotoxic chemotherapy (adriamycin, cyclophosphamide, mitomycin-C and 5-FU) as offered by her local oncologist. She was started on weekly IV administration of cisplatin in combination with adriamycin and other agents. The patient suffered no side effects except hair loss and fatigue the day of infusion. Subsequent examinations have demonstrated re-ossification of bone metastasis, elimination of ascites, elimination of palpable abdominal masses, disappearance of the liver mass and weight gain.

EXAMPLE 50

Acemannan Treatment of Cutaneous Fungal Infections

A 40-year-old physician applied acemannan gel to itching, cracked, and burning lesions between and above the bases of his toes. In less than a week, the doctor reported that the response and healing proved acemannan to be the most effective medication he had used in over 20 years of periodic treatment of his chronic athlete's foot. Other patients have reported similar improvement. Remarkably, some patients who were taking acemannan for other conditions reported improvement of athlete's foot lesions.

EXAMPLE 51

Acemannan Treatment of Marine Animal Stings

A 40-year-old female who was scuba diving damaged her knee on fire coral. The lesions covered approximately 9 square centimeters of skin surface. The normal clinical course of this sting in humans is intense inflammation for approximately 8 hours followed by delayed healing of the skin wound for 14 days. Application of acemannan gel to the wound for 8 days resulted in complete healing, and scarring was barely detectable.

SUMMARY

Acemannan has been shown to be effective in treating a number of conditions where the principal mechanism of resolution or cure requires intervention by the patient's immune system. Acemannan has direct stimulatory effects on the immune system. In addition, acemannan directly interacts with virus or other infectious organisms, infected cells, and tumor cells to produce changes in their immunologically sensitive surface composition to alter the appearance of these agents and cause them to be recognized by the body's immune system and then destroyed.

It is thus believed that the operation and administration of the present invention will be apparent from the foregoing description. While the method and techniques shown and described have been characterized as being preferred, it will be obvious that various changes and modifications may be made therein without departing from the spirit and scope of the invention as defined in the following claims.

We claim:

1. A method for treating an animal having a tumor selected from the group consisting of sarcoma, carcinoma and lymphoma, said method comprising:

administering to said animal an amount of a acetylated mannan derivative sufficient to inhibit the growth of said tumor.

2. The method according to claim 1, wherein said animal comprises a human, a domesticated animal, a farm animal, or a bird.

3. The method according to claim 1, wherein said tumor comprises benign tumor or malignant tumor.

4. The method according to claim 1, wherein said tumor comprises sarcoma.

5. The method according to claim 1, wherein said tumor comprises carcinoma.

6. The method according to claim 1, wherein said tumor comprises lymphoma.

* * * * *

UNITED STATES PATENT AND TRADEMARK OFFICE
CERTIFICATE OF CORRECTION

PATENT NO. : 5,773,425
DATED : June 30, 1998
INVENTOR(S) : McAnalley, et al

It is certified that error appears in the above-indentified patent and that said Letters Patent is hereby corrected as shown below:

Col. 12, line 42 "4,735;935" should be --4,735,935--;

Col. 16, line 37 "hosts" should be --host.--;

Col. 18, line 59 "allquots" should be --aliquots--;

Col. 19, line 14 "Tlymocytes" should be --Thymocytes--;

Col. 19, line 26 "0.5 µg/well" should be --0.5µCi/well--;

Col. 26, line 19 "51CR" should be --$^{51}$CR--;

Col. 32, line 15 please insert --in-- between of and Vitro;

Col. 33, line 24 "10%. Together the" should be --10% together. The--;

Col. 34, line 29 "patients" should be --Patients--;

Col. 35, line 16 "dependent" should be --Dependent--;

Col. 35, line 39 "µ/ml" should be --µg/ml--;

Col. 39, line 31 "5" should be --Five--;

Col. 45, line 54 "319%" should be --31%--;

Col. 50, line 22 "cat" should be --eat--;

Col. 50, line 40 "drug" should be --Drug--;

Col. 50, line 62 "drug" should be --Drug--; and

UNITED STATES PATENT AND TRADEMARK OFFICE
CERTIFICATE OF CORRECTION

PATENT NO. : 5,773,425
DATED : June 30, 1998
INVENTOR(S) : McAnalley et al.

It is certified that error appears in the above-identified patent and that said Letters Patent is hereby corrected as shown below:

Col. 56, line 1 "(rofbutin)" should be --(rifbutin)--.

Signed and Sealed this

First Day of December, 1998

Attest:

BRUCE LEHMAN

Attesting Officer

Commissioner of Patents and Trademarks